US012075988B2

(12) United States Patent
Gordon

(10) Patent No.: US 12,075,988 B2
(45) Date of Patent: Sep. 3, 2024

(54) TELESCOPING BIOPSY NEEDLE

(71) Applicant: INTUITIVE SURGICAL OPERATIONS, INC., Sunnyvale, CA (US)

(72) Inventor: Lucas S. Gordon, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 561 days.

(21) Appl. No.: 17/096,514

(22) Filed: Nov. 12, 2020

(65) Prior Publication Data
US 2021/0204920 A1 Jul. 8, 2021

Related U.S. Application Data

(63) Continuation of application No. 15/103,841, filed as application No. PCT/US2014/069959 on Dec. 12, 2014, now Pat. No. 10,856,855.
(Continued)

(51) Int. Cl.
A61B 10/02 (2006.01)
A61B 10/04 (2006.01)
A61B 34/20 (2016.01)

(52) U.S. Cl.
CPC .......... A61B 10/0233 (2013.01); A61B 10/04 (2013.01); A61B 34/20 (2016.02);
(Continued)

(58) Field of Classification Search
CPC ..... A61B 10/0233; A61B 34/20; A61B 10/04; A61B 2034/2061; A61B 10/0283; A61B 2010/045
See application file for complete search history.

(56) References Cited

U.S. PATENT DOCUMENTS 4,617,940 A 10/1986 Wang
4,750,475 A 6/1988 Yoshihashi
(Continued)

FOREIGN PATENT DOCUMENTS

CN 88211372 U 12/1988
CN 1221603 A 7/1999
(Continued)

OTHER PUBLICATIONS

Extended European Search Report for Application No. 14870446.3, mailed on Jul. 31, 2017, 6 pages.
(Continued)

Primary Examiner — Daniel L Cerioni
(74) Attorney, Agent, or Firm — Haynes & Boone, LLP

(57) ABSTRACT

A medical device comprises an elongate sheath comprising a distal portion and a proximal portion and defining a first lumen. The medical device further comprises an elongate instrument slidably disposed at least partially within the first lumen. The elongate instrument comprises a rigid distal section defining a second lumen. The medical device further comprises a first extension member coupled to a proximal end of the elongate instrument and a second extension member coupled to a proximal end of the elongate sheath. The second extension member is configured to at least partially receive the elongate instrument. The medical device further comprises a holding mechanism coupled to the second extension member. The holding mechanism includes a protrusion configured to maintain the elongate instrument in a rotationally fixed position relative to the distal portion of the elongate sheath.

16 Claims, 16 Drawing Sheets

Related U.S. Application Data

(60) Provisional application No. 61/915,950, filed on Dec. 13, 2013.

(52) U.S. Cl.
CPC ..... *A61B 10/0283* (2013.01); *A61B 2010/045* (2013.01); *A61B 2034/2061* (2016.02)

(56) References Cited

U.S. PATENT DOCUMENTS

| | | | |
|---|---|---|---|
| 4,973,317 A | 11/1990 | Bobrove | |
| 5,201,721 A * | 4/1993 | Lee | A61M 5/3271 |
| | | | 604/263 |
| 6,380,732 B1 | 4/2002 | Gilboa | |
| 6,389,187 B1 | 5/2002 | Greenaway et al. | |
| 6,592,581 B2 | 7/2003 | Bowe | |
| 7,037,290 B2 | 5/2006 | Gardeski et al. | |
| 8,282,575 B2 | 10/2012 | Tonomura et al. | |
| 8,603,071 B2 | 12/2013 | Nimgaard et al. | |
| 8,900,131 B2 | 12/2014 | Chopra et al. | |
| 10,856,855 B2 | 12/2020 | Gordon | |
| 2001/0011161 A1 | 8/2001 | Edwards et al. | |
| 2005/0090764 A1 | 4/2005 | Wang | |
| 2005/0119652 A1 | 6/2005 | Vetter et al. | |
| 2005/0159728 A1 | 7/2005 | Armour et al. | |
| 2005/0180389 A1 | 8/2005 | Xenakis et al. | |
| 2006/0013523 A1 | 1/2006 | Childers et al. | |
| 2007/0065077 A1 | 3/2007 | Childers et al. | |
| 2008/0221391 A1* | 9/2008 | Weitzner | A61B 1/00154 |
| | | | 604/524 |
| 2008/0249436 A1 | 10/2008 | Darr | |
| 2010/0105979 A1 | 4/2010 | Hamel et al. | |
| 2010/0312141 A1* | 12/2010 | Keast | A61B 8/12 |
| | | | 600/567 |
| 2012/0071822 A1* | 3/2012 | Romo | A61B 6/4423 |
| | | | 604/95.04 |
| 2012/0191007 A1* | 7/2012 | Buressiniani | A61B 10/0233 |
| | | | 600/566 |
| 2013/0096377 A1 | 4/2013 | Duindam et al. | |
| 2013/0184732 A1 | 7/2013 | Tanaka et al. | |
| 2013/0204124 A1 | 8/2013 | Duindam et al. | |
| 2013/0225996 A1 | 8/2013 | Dillard et al. | |
| 2013/0253370 A1 | 9/2013 | Vetter et al. | |
| 2013/0296691 A1 | 11/2013 | Ashe | |
| 2014/0257253 A1* | 9/2014 | Jemison | A61B 17/00234 |
| | | | 606/1 |
| 2016/0151122 A1 | 6/2016 | Alvarez et al. | |
| 2016/0331358 A1 | 11/2016 | Gordon | |

FOREIGN PATENT DOCUMENTS

| | | |
|---|---|---|
| CN | 1708325 A | 12/2005 |
| CN | 203017047 U | 6/2013 |
| CN | 103284763 A | 9/2013 |
| EP | 2614778 A2 | 7/2013 |
| JP | 2001070307 A | 3/2001 |
| JP | 2007020868 A | 2/2007 |
| WO | WO-2011160445 A1 | 12/2011 |

OTHER PUBLICATIONS

International Preliminary Report on Patentability for Application No. PCT/US2014/069959, mailed on Jun. 23, 2016, 12 pages.

International Search Report and Written Opinion for Application No. PCT/US14/69959, mailed on Apr. 2, 2015, 19 pages.

Office Action mailed Aug. 15, 2019 for Chinese Application No. CN201480074860 filed Dec. 12, 2014, 24 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

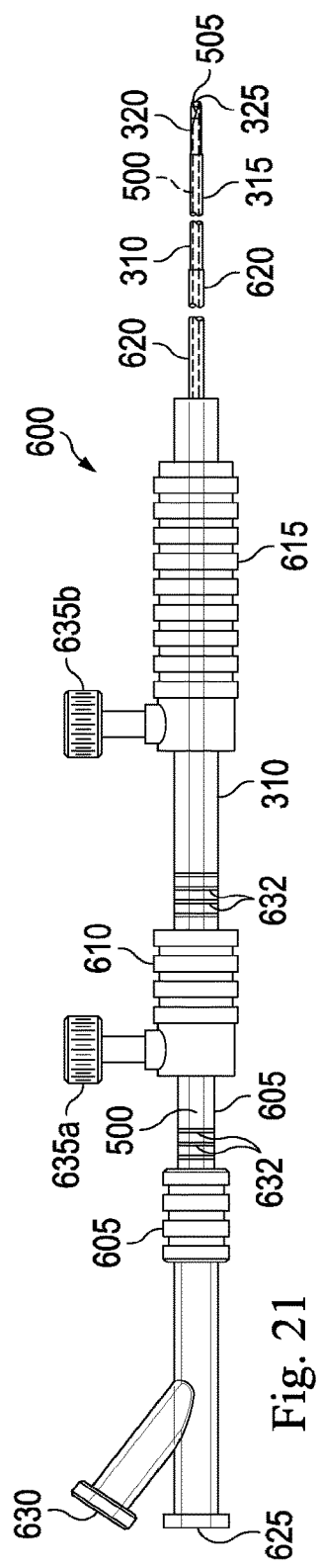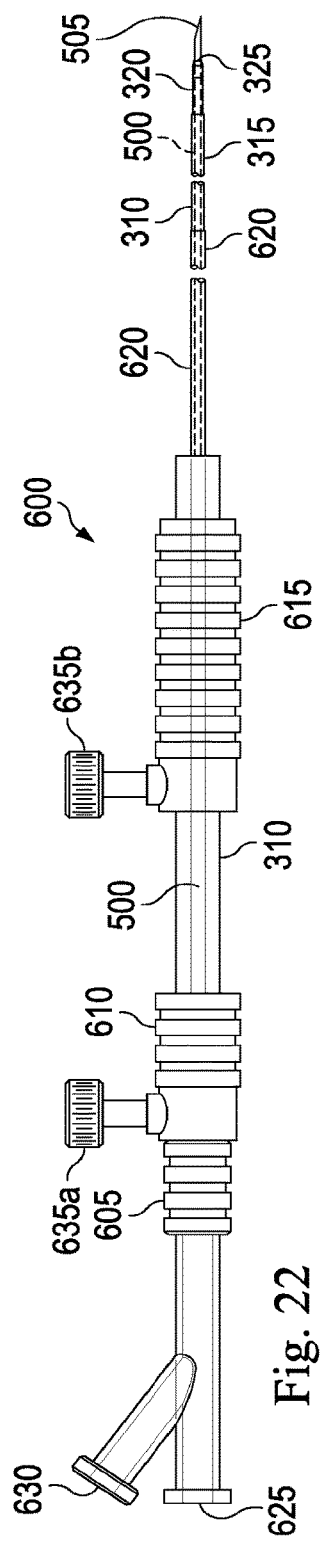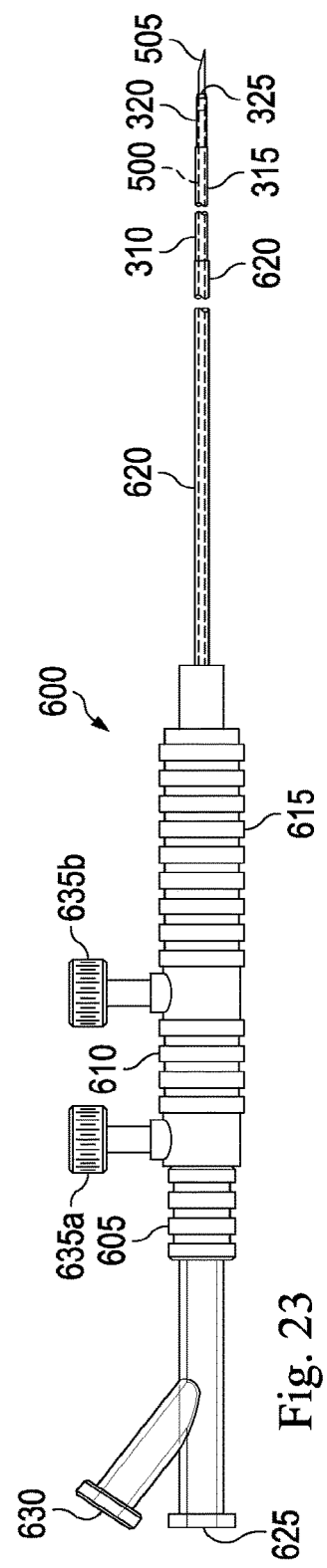

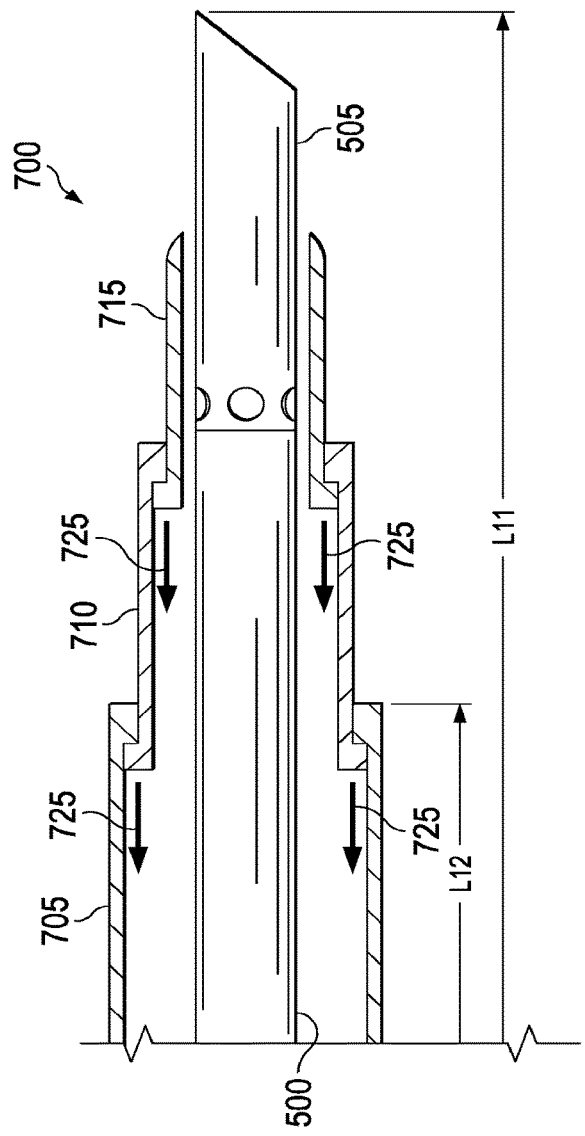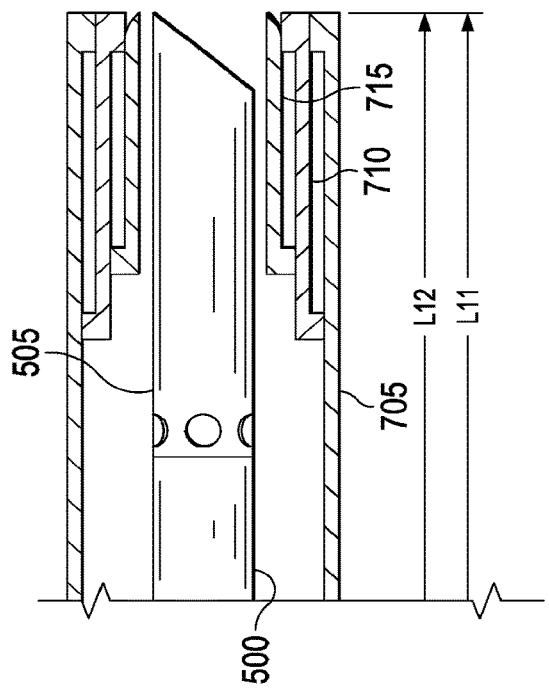

TELESCOPING BIOPSY NEEDLE

RELATED APPLICATIONS

This application is a continuation application of U.S. patent application Ser. No. 15/103,841, filed Jun. 10, 2016, which is the U.S. national phase of International Application No. PCT/US2014/069959, filed Dec. 12, 2014, which designated the U.S. and claims priority to and the benefit of U.S. Provisional Patent Application No. 61/915,950, filed Dec. 13, 2013, all of which are incorporated herein by reference in their entirety.

FIELD

The present disclosure is directed to systems and methods for navigating a patient anatomy to conduct a minimally invasive procedure, and more particularly to apparatus and methods for obtaining a targeted tissue biopsy using a low-profile, telescoping, flexible medical instrument.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Clinicians may insert medical tool through these natural orifices or incisions to reach a target tissue location. Medical tools include instruments such as therapeutic instruments, diagnostic instruments, and surgical instruments. To reach the target tissue location, a minimally invasive medical tool may navigate natural or surgically created passageways in anatomical systems such as the lungs, the colon, the intestines, the kidneys, the heart, the circulatory system, or the like.

Minimally invasive surgical procedures typically rely on some sort of instrument position monitoring to ensure proper access to, and behavior at, the target tissue location. Conventional minimally invasive surgical instruments are generally either formed from generally rigid, elongate elements (e.g., laparoscopic or robotic systems) or highly flexible systems designed to follow a predetermined anatomic path (e.g., angioplasty balloon catheters). In either case, position monitoring typically involves localized tracking of a discrete portion of the instrument (e.g., the distal tip of a catheter). The remaining guidewire/catheter length is not actively monitored, except in an incidental sense to the extent the remaining length is shown during fluoroscopic visualization of the tip advancement.

However, increasingly more complex minimally invasive surgical systems can require enhanced instrument position monitoring for safe and effective use. For example, the development of flexible, steerable needles provides an opportunity for procedures such as biopsy and/or therapeutic treatment, such as ablation treatments or radioactive seeds placement, at internal locations that would be problematic to access via a straight path (e.g., in situations where it would be undesirable to puncture any intervening anatomy). Flexible, steerable needles can be delivered to the target site by direct penetration into the tissue, such as for example in the case of transcutaneous biopsy needles for the liver or other internal organs. In other instances, flexible, steerable needles can be delivered to the target site through the lumen of an endoscope or a catheter, such as for example in the case of transluminal lung or stomach biopsies.

The use and positional tracking of a flexible needle in a minimally invasive fashion can be significantly more complicated than conventional robotic or laparoscopic procedures. Not only is the variability in the actual shape of a steerable needle much greater than that of a linkage of rigid elements, but the needle flexibility can greatly increase susceptibility to deviation from a target trajectory due to variations in tissue characteristics (e.g., scar tissue, or otherwise denser than expected tissue, may result in greater than expected curvature of the flexible needle). Thus, accurately guiding and tracking the position of a flexible needle poses unique difficulties.

Accordingly, it is desirable to provide a steerable flexible needle system that can be effectively guided and tracked during minimally invasive surgical procedures. The devices, systems, and methods disclosed herein overcome one or more of the deficiencies of the prior art.

SUMMARY

The embodiments of the invention are summarized by the claims that follow the description.

In one embodiment, the present disclosure describes a medical device including an elongate sheath, an elongate instrument, and a holding mechanism. The elongate sheath defines a first lumen, and includes a rigid distal portion and a flexible proximal portion. The elongate instrument includes a rigid distal section that defines a second lumen. The elongate instrument is slidably disposed at least partially within the first lumen of the elongate sheath. The elongate instrument can be extended relative to the elongate sheath. In an extended configuration, the rigid distal section of the elongate instrument is in an extended position from the rigid distal portion of the elongate sheath. The holding mechanism operates to maintain the rigid distal section in this extended position from the rigid distal portion.

In another embodiment, the present disclosure describes a method of operating a medical device. The method involves navigating an elongate sheath with a rigid distal portion through a tortuous pathway to an anatomical tissue of interest. Upon reaching the anatomical tissue of interest, an elongate instrument with a rigid distal section is extended from a lumen of the elongate sheath. The rigid distal section is then maintained in an extended position from the rigid distal portion, and the rigid distal section and the rigid distal portion are inserted into the anatomical tissue of interest.

In another embodiment, the present disclosure describes a minimally invasive system comprising an elongate sheath and an elongate instrument. In one aspect, the elongate sheath extends from a proximal end to a distal end and includes a flexible proximal portion, a rigid distal portion, and a lumen. In one aspect, the lumen extends through the flexible proximal portion and the rigid distal portion and defines a longitudinal axis of the sheath. In one aspect, the flexible proximal portion is fixedly coupled to the rigid distal portion. In one aspect, the elongate instrument is slidably disposed within the lumen of the sheath. In one aspect, the elongate instrument includes a rigid distal section, and is movable within the sheath between a retracted condition in which the rigid distal section of the instrument is retracted within the rigid distal portion of the sheath and an extended configuration in which the rigid distal section of the medical instrument at least partially extends from the rigid distal portion of the sheath.

In another embodiment, the present disclosure describes a minimally invasive system comprising an elongate sheath and a needle. In one aspect, the elongate sheath extends from a proximal end to a distal end and includes a flexible proximal portion, a rigid distal portion, and a lumen. In one aspect, the flexible proximal portion is fixedly coupled to the rigid distal portion. In one aspect, the lumen extends through the flexible proximal portion and the rigid distal portion and defines a longitudinal axis of the sheath. In one aspect, the needle includes a flexible proximal section and a rigid distal section. In one aspect, the needle is slidably disposed within the lumen of the sheath, and the needle is movable within the sheath between a retracted condition in which the rigid distal section of the needle is retracted within the rigid distal portion of the sheath and an extended configuration in which at least the rigid distal section of the needle extends from the distal end of the sheath.

In another embodiment, the present disclosure describes a minimally invasive system comprising an elongate sheath and an elongate instrument. In one aspect, the elongate sheath extends from a proximal end to a distal end and includes a flexible tube portion, a sheath element, a rigid tube section, and a lumen. In one aspect, the flexible tube portion is fixedly coupled to a distal end of the sheath element, and the rigid tube section is fixedly coupled to a distal end of the flexible tube. In one aspect, the lumen extends through the sheath element, the flexible tube portion, and the rigid tube section to define a longitudinal axis of the sheath. In one aspect, the elongate instrument is slidably disposed within the lumen of the sheath, and the instrument includes a rigid distal portion adapted to move between a retracted configuration in which the rigid distal portion is retracted within the rigid tube section of the sheath and an extended configuration in which the rigid distal portion at least partially extends from the rigid tube section of the sheath.

In another embodiment, the present disclosure describes a minimally invasive instrument system comprising an elongate flexible sheath, a needle, and a sensor element. In one aspect, the sheath extends from a proximal end to a distal end and includes a flexible proximal portion, a rigid distal portion, and a lumen extending through the flexible proximal portion and the distal rigid portion and defining a longitudinal axis of the sheath. In one aspect, the needle includes a needle lumen and is slidably disposed within the lumen of the sheath. In one aspect, the needle includes a flexible proximal section and a rigid distal section, and the needle is movable between a retracted condition with the rigid distal section telescopically received within the rigid distal portion of the sheath and an extended condition with the rigid distal section extending distally from the rigid distal portion of the sheath. In one aspect, the sensor element is disposed within the needle lumen. In one aspect, the system comprises an actuator configured to manipulate the needle and the elongate flexible sheath.

In another embodiment, the present disclosure describes a method of obtaining a biopsy sample from target tissue in a patient in a minimally invasive procedure, comprising positioning a distal end of a flexible needle system adjacent an anatomical area of interest. In one aspect, the flexible needle system comprises a needle slidably disposed within an outer sheath having a common lumen extending through a flexible proximal portion and a rigid distal portion, and the needle includes a rigid distal section, a lumen in fluid communication with the rigid distal section, and housing a sensor system coaxially aligned with the lumen. In one aspect, the method comprises evaluating the sensed position of the needle, and advancing a proximal end of the needle through the outer sheath based on the sensed position in the direction of the target tissue until the rigid distal section of the needle emerges distal of the rigid distal portion and penetrates the target tissue. In one aspect, the method comprises advancing a distal end of the outer sheath over the rigid distal section of the needle as the needle is advanced. In one aspect, the method comprises advancing the needle based on the sensed position toward the target tissue. In one aspect, the method comprises obtaining the biopsy sample through the rigid distal section of the needle.

Additional aspects, features, and advantages of the present disclosure will become apparent from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 3A:
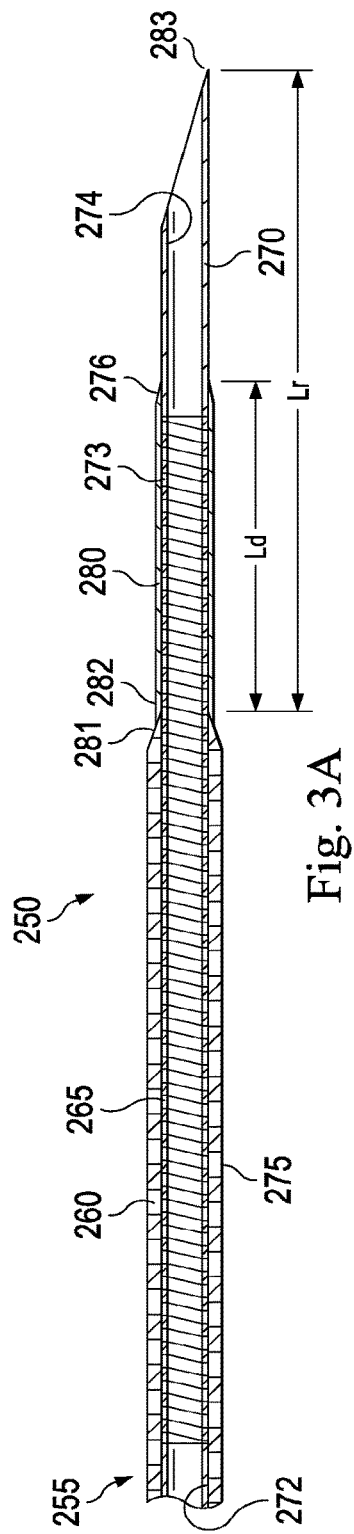
Figure 3B:
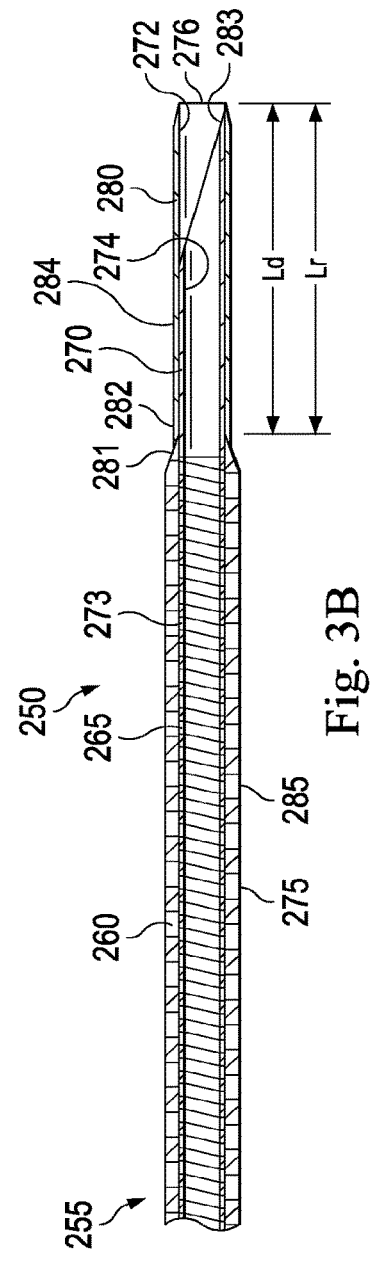
Figure 3C:
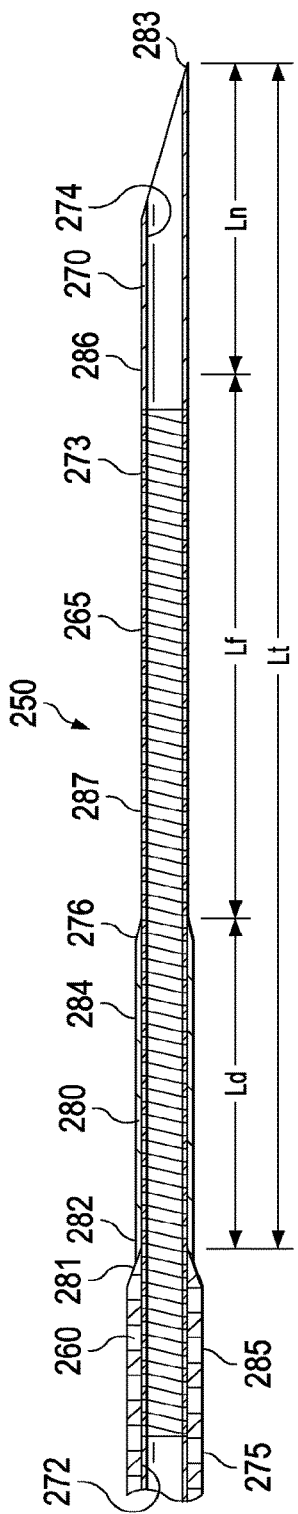

FIGS. 3A-3C illustrate a distal portion an exemplary steerable, flexible needle system having an exemplary needle and an exemplary outer sheath in accordance with an embodiment of the present disclosure. FIG. 3A illustrates the exemplary needle positioned in a partially extended condition within the exemplary outer sheath. FIG. 3B illustrates the exemplary needle positioned in a retracted condition within the exemplary outer sheath. FIG. 3C illustrates the exemplary needle positioned in a fully extended condition relative to the outer sheath.

Figure 4:
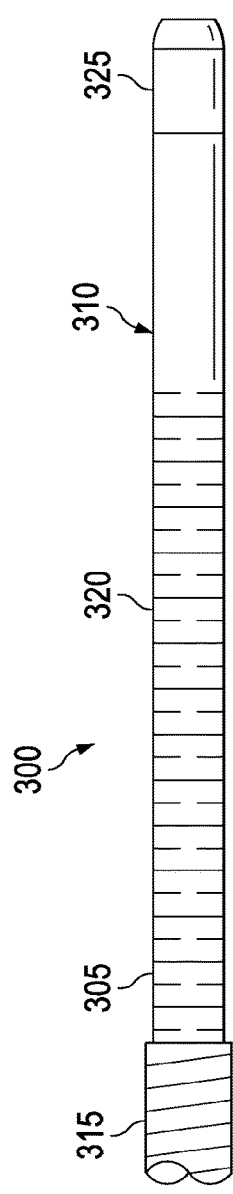

FIG. 4 illustrates a distal portion of an exemplary steerable, flexible needle system in accordance with an embodiment of the present disclosure.

Figure 5:
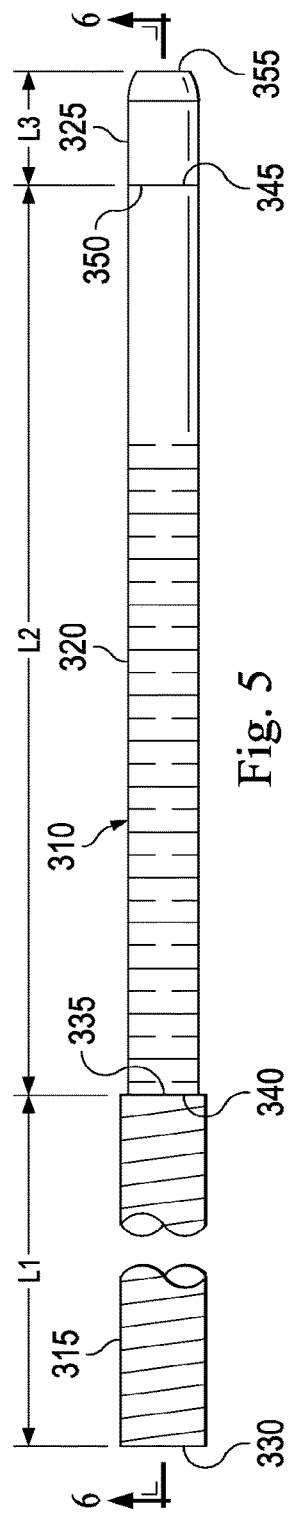

FIG. 5 illustrates a diagrammatic side view of an exemplary outer sheath of the needle system shown in FIG. 4 in accordance with an embodiment of the present disclosure.

Figure 6:
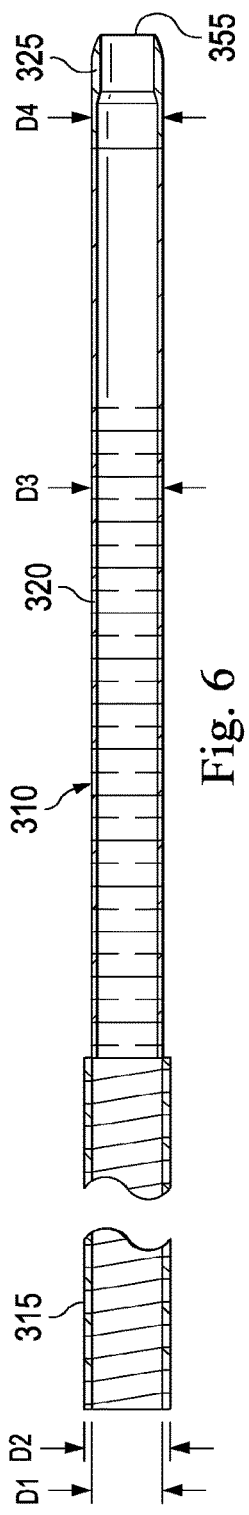

FIG. 6 illustrates a diagrammatic cross-sectional view of the outer sheath shown in FIG. 4 in accordance with an embodiment of the present disclosure.

Figure 7:
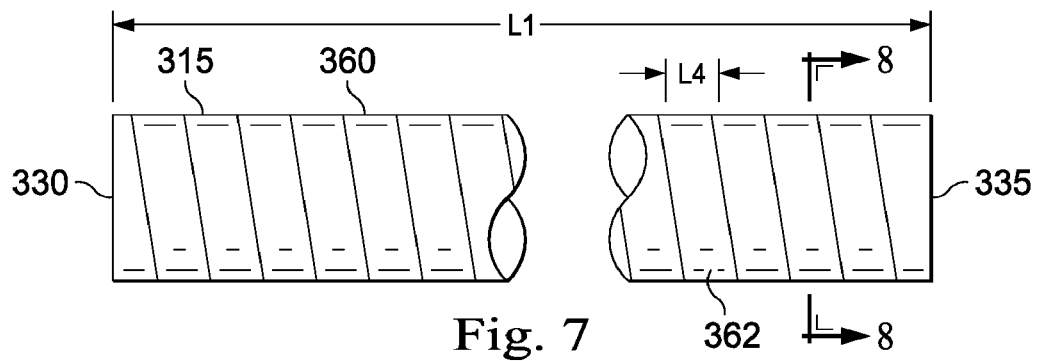

FIG. 7 illustrates a diagrammatic side view of an exemplary coil sheath of the outer sheath shown in FIG. 6 in accordance with an embodiment of the present disclosure.

Figure 8:
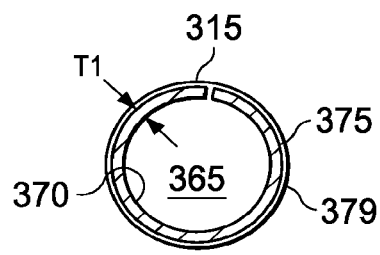

FIG. 8 illustrates a diagrammatic cross-sectional view of the coil sheath along the line 8-8 shown in FIG. 7 in accordance with an embodiment of the present disclosure.

Figure 9:
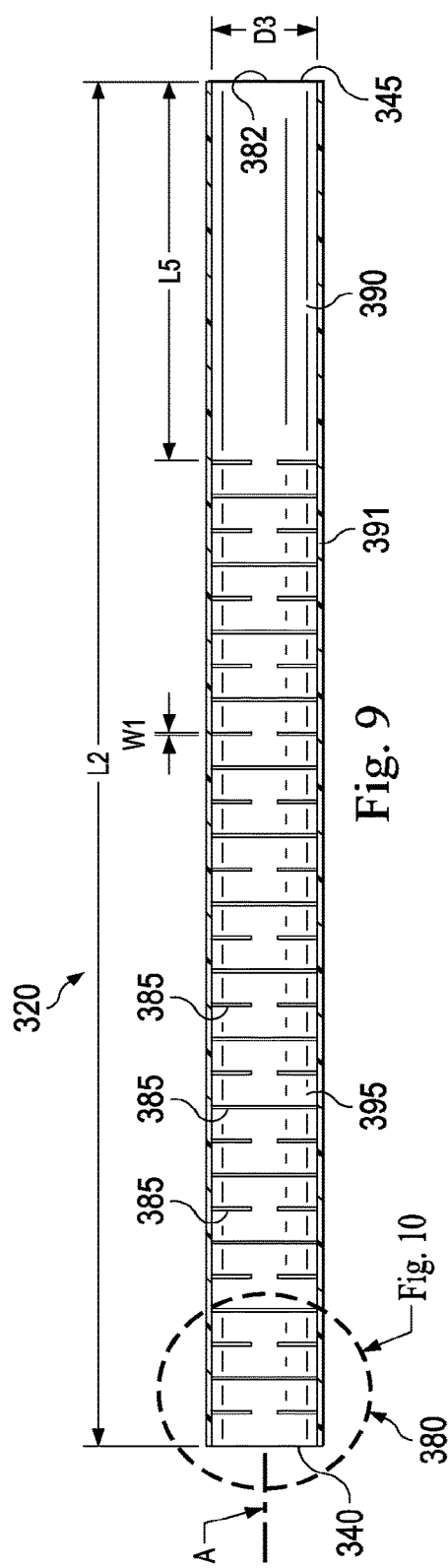

FIG. 9 illustrates a diagrammatic side view of an exemplary elongate tube of the outer sheath shown in FIG. 6 in accordance with an embodiment of the present disclosure.

Figure 10:
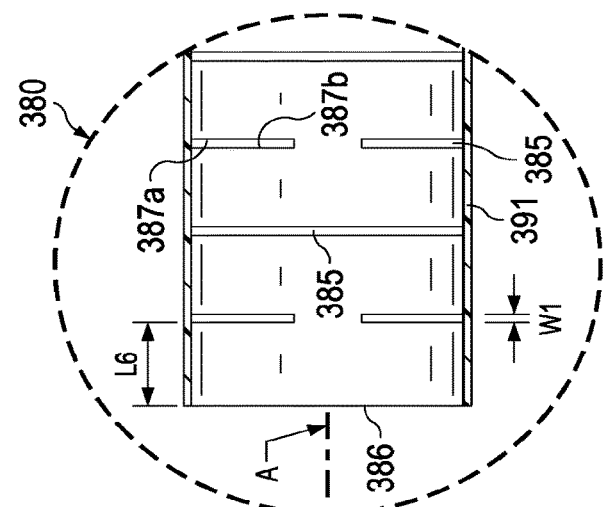

FIG. 10 illustrates a diagrammatic side view of an enlarged portion of the elongate tube shown in FIG. 9.

Figure 11:
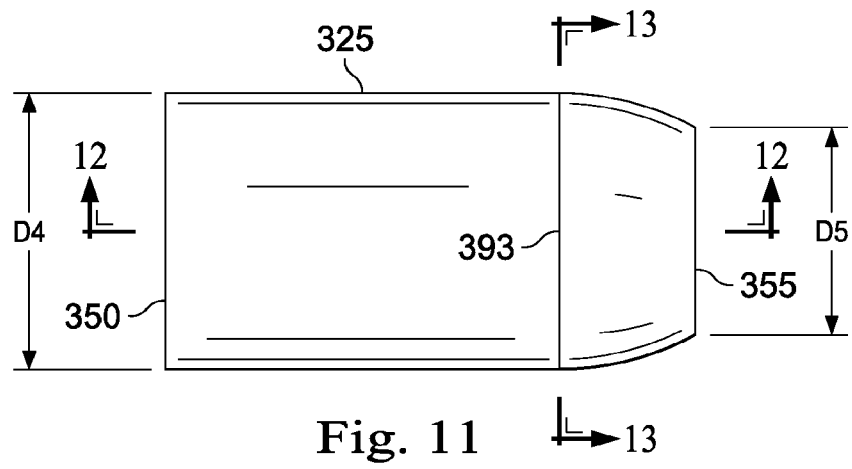

FIG. 11 illustrates a diagrammatic side view of an exemplary sheath tip of the outer sheath shown in FIG. 6 in accordance with an embodiment of the present disclosure.

Figure 12:
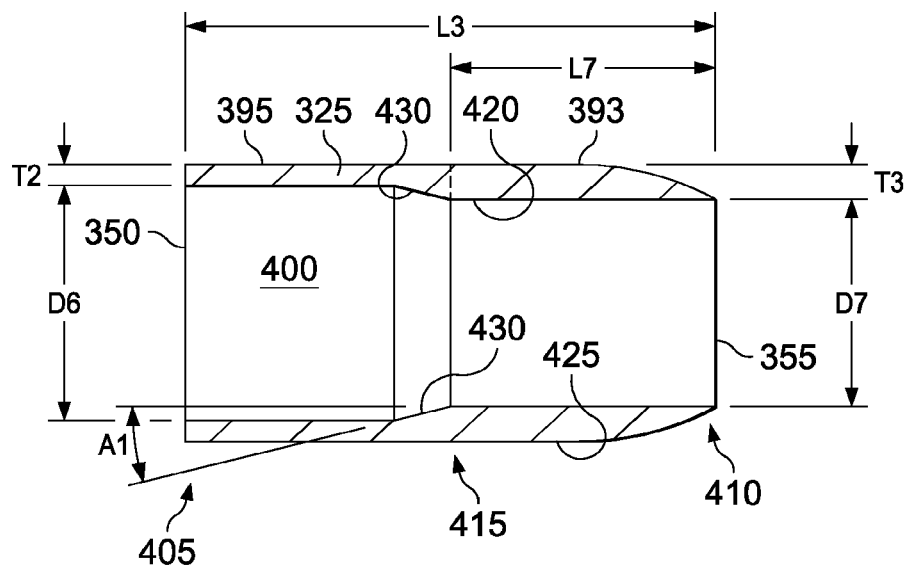

FIG. 12 illustrates a diagrammatic cross-sectional view of the sheath tip along the line 12-12 shown in FIG. 11.

Figure 13:
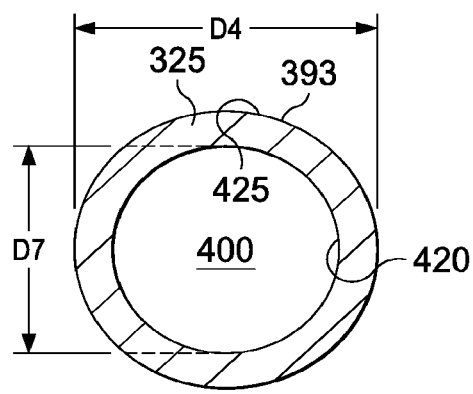

FIG. 13 illustrates a diagrammatic cross-sectional view of the sheath tip along the line 13-13 shown in FIG. 11.

Figure 14:
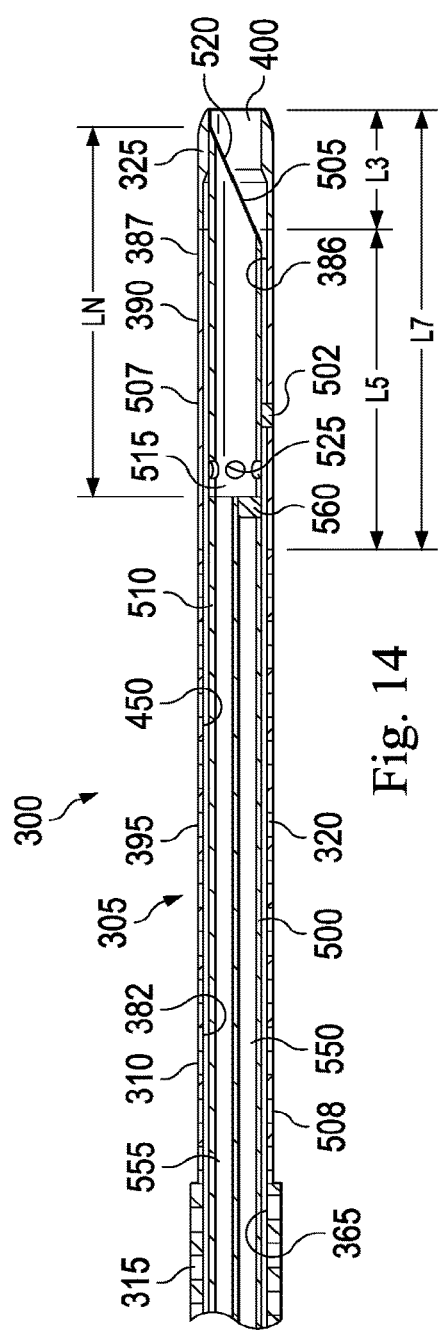

FIG. 14 illustrates a partially cross-sectional side view of a distal portion of the exemplary steerable, flexible needle system shown in FIG. 4 in accordance with an embodiment of the present disclosure. FIG. 14 illustrates an exemplary needle of the needle system in a non-advanced or un-extended position within the exemplary outer sheath.

Figure 15:
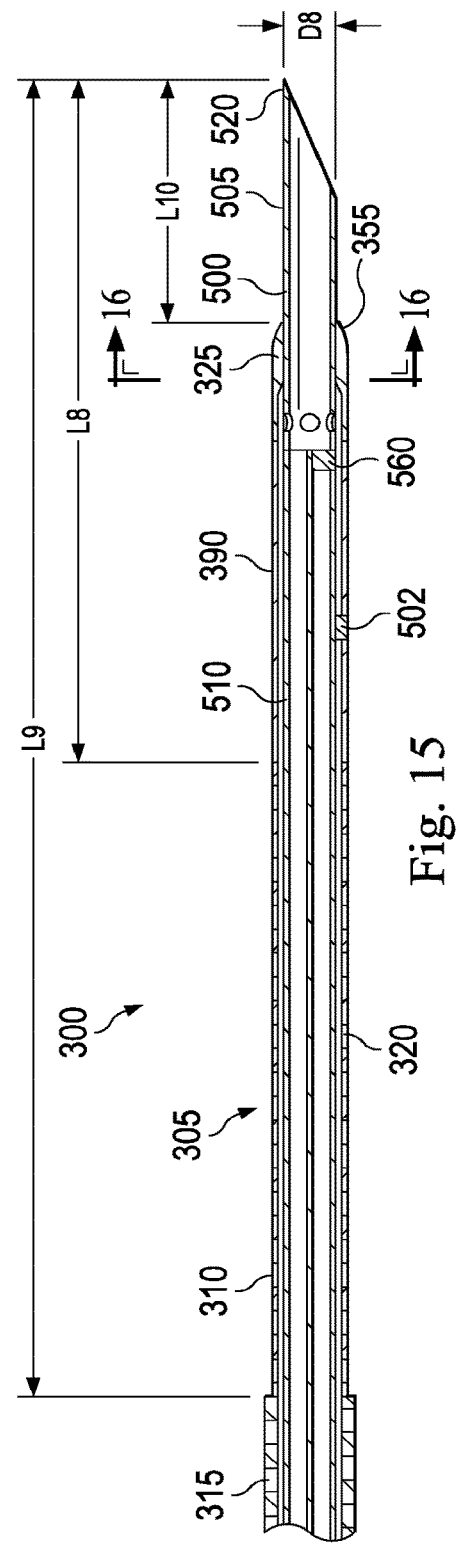

FIG. 15 illustrates a partially cross-sectional side view of a distal portion of the exemplary steerable, flexible needle system shown in FIG. 14 with the exemplary needle in an advanced or extended position relative to the exemplary outer sheath.

Figure 16:
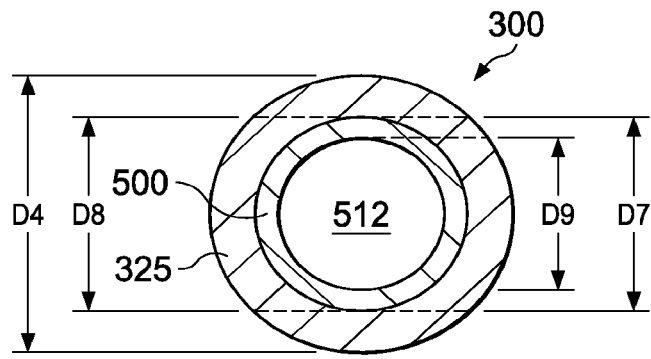

FIG. 16 illustrates a diagrammatic cross-sectional view of the exemplary sheath tip and the exemplary needle along the line 16-16 shown in FIG. 15.

Figure 17:
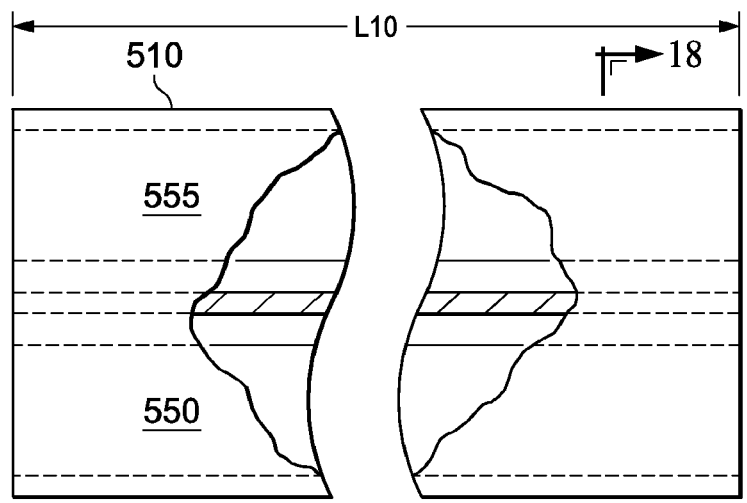

FIG. 17 illustrates a diagrammatic side view of an exemplary needle jacket of the exemplary needle shown in FIG. 14 in accordance with an embodiment of the present disclosure.

Figure 18:
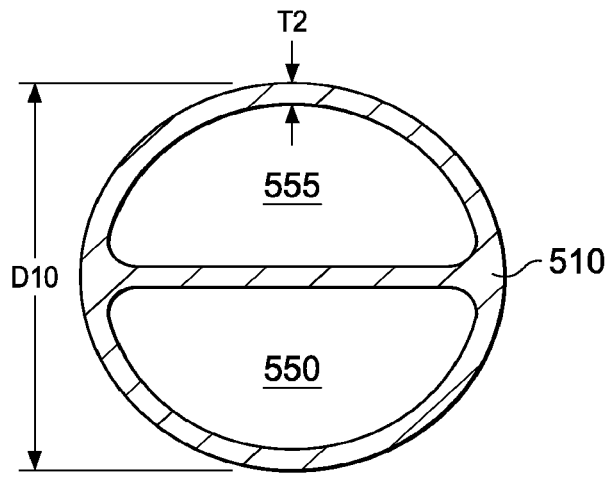

FIG. 18 illustrates a diagrammatic cross-sectional view of the exemplary needle jacket along the line 18-18 shown in FIG. 17.

Figure 19A:
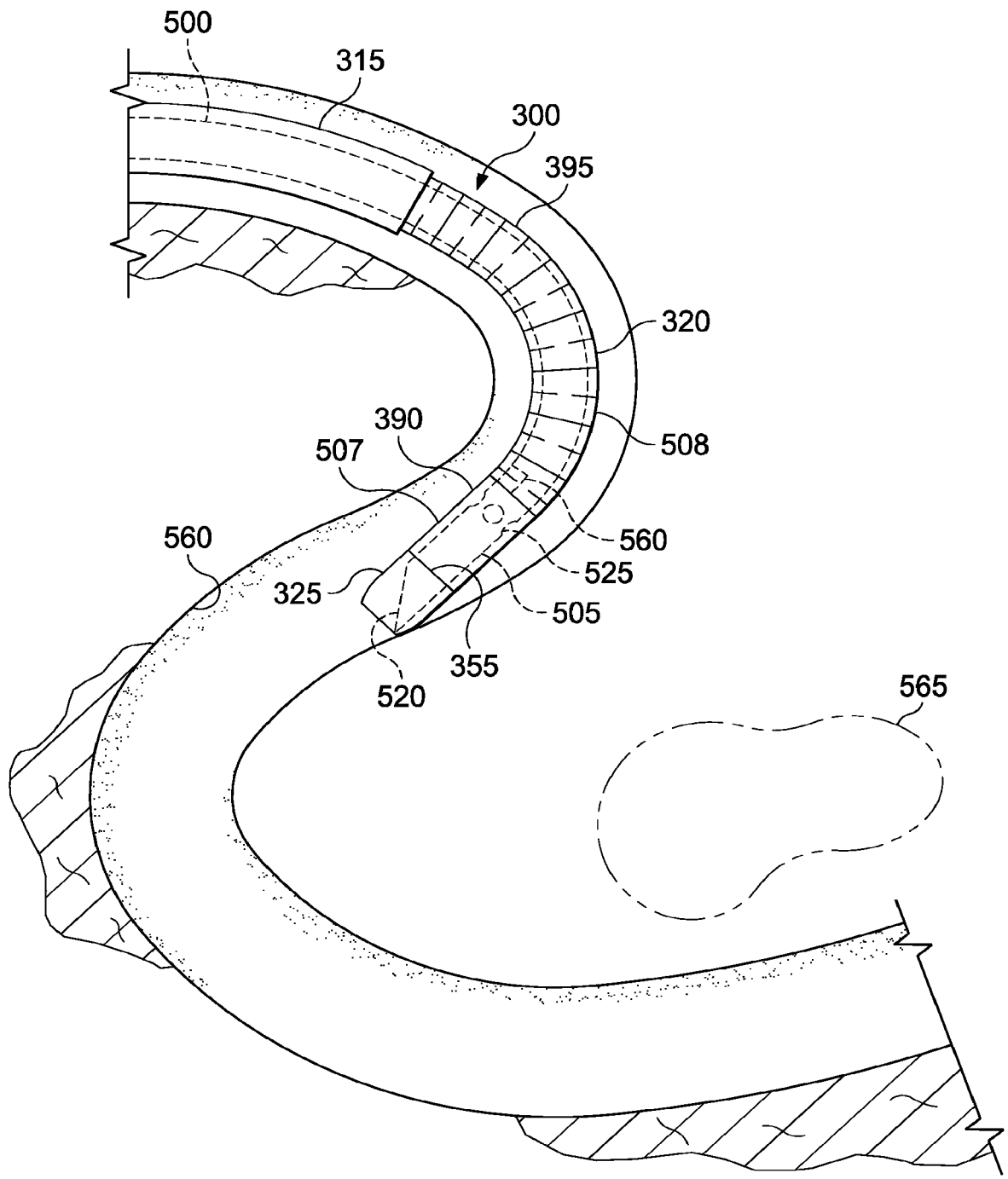

FIG. 19A illustrates a diagrammatic view of the exemplary needle system shown in FIG. 14 navigating a tortuous pathway (i.e., within a patient's anatomy) in accordance with an embodiment of the present disclosure.

Figure 19B:
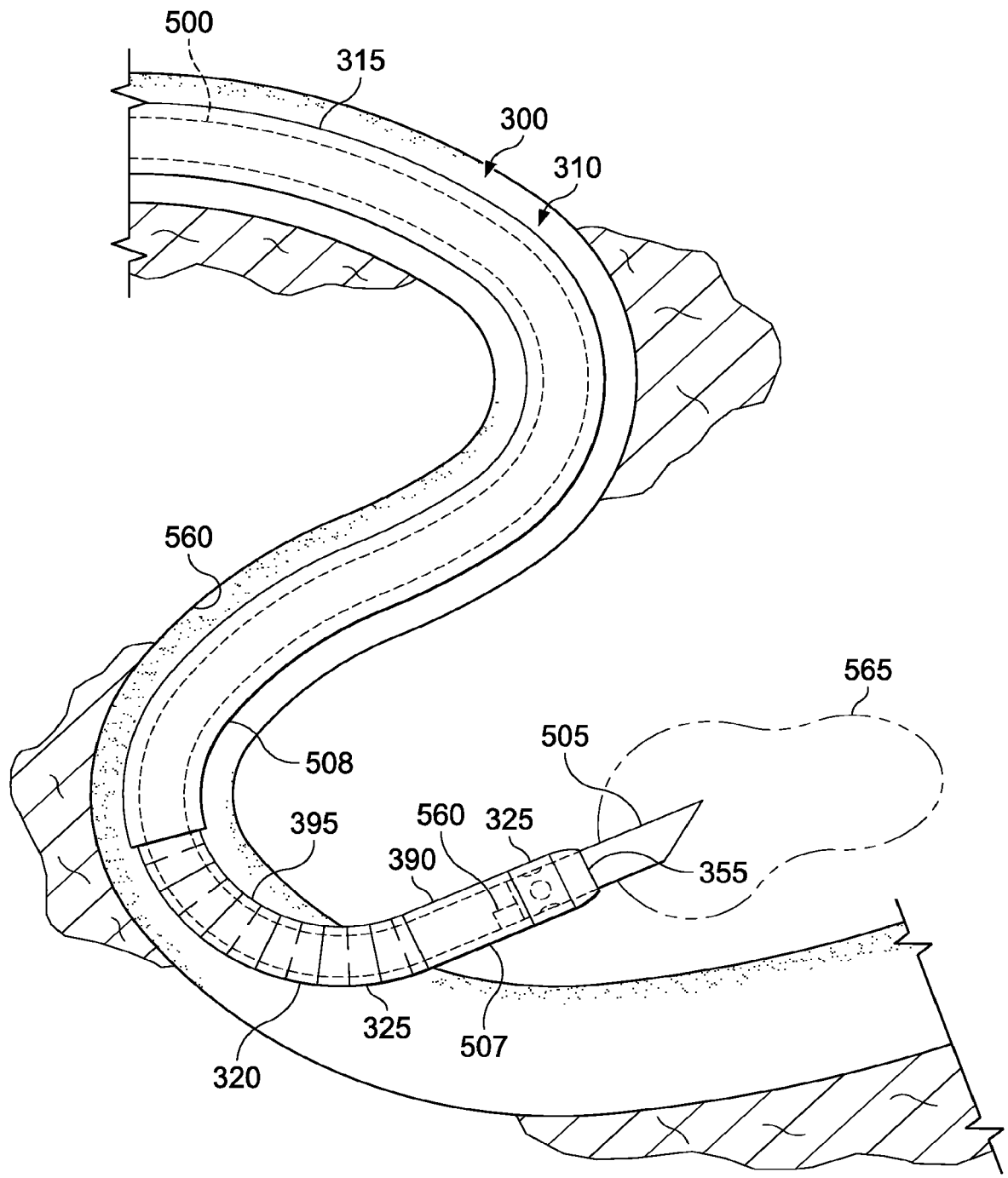

FIG. 19B illustrates a diagrammatic view of the exemplary needle system shown in FIG. 14 obtaining a biopsy sample (i.e., at a target area within a patient's anatomy) in accordance with an embodiment of the present disclosure.

Figure 20A:
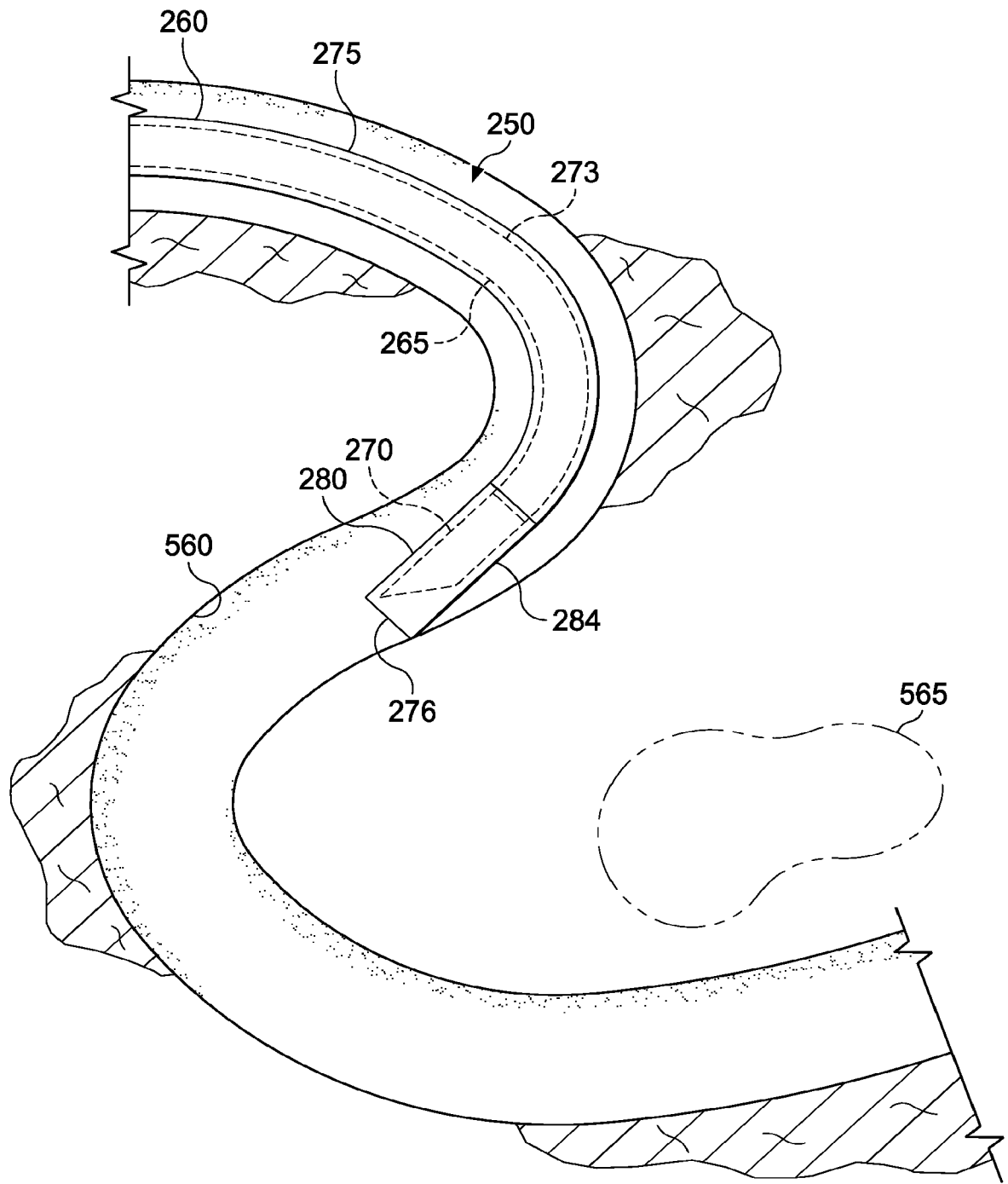

FIG. 20A illustrates a diagrammatic view of the exemplary needle system shown in FIGS. 3A-3C navigating a tortuous pathway (i.e., within a patient's anatomy) in accordance with an embodiment of the present disclosure.

Figure 20B:
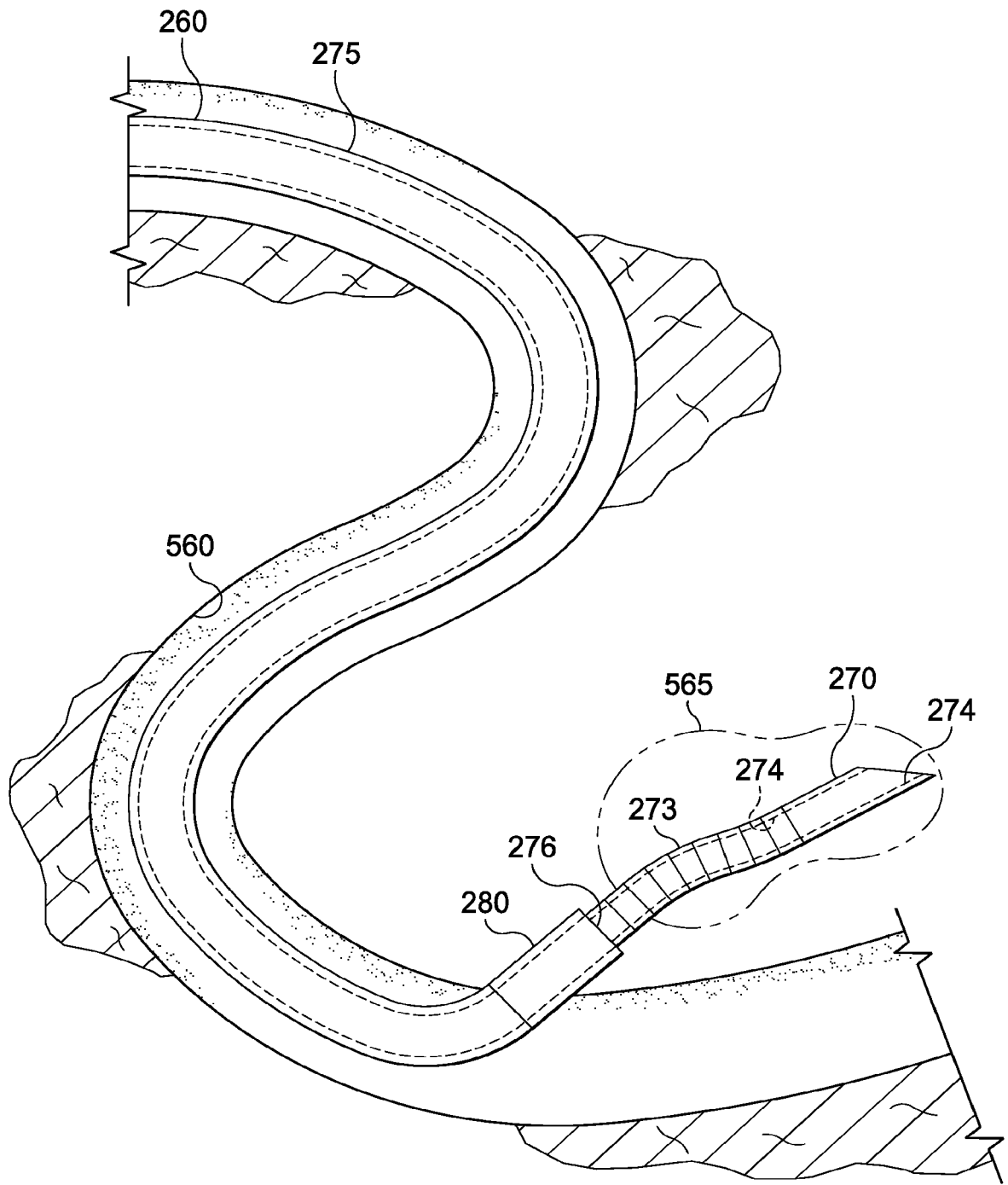

FIG. 20B illustrates a diagrammatic view of the exemplary needle system shown in FIGS. 3A-3C obtaining a biopsy sample (i.e., at a target area within a patient's anatomy) in accordance with an embodiment of the present disclosure.

FIG. 21 illustrates a partially cross-sectional side view of an exemplary proximal portion of the needle system shown in FIG. 14. The exemplary needle and the exemplary outer sheath are shown in an un-advanced or un-extended position.

FIG. 22 illustrates a partially cross-sectional side view of an exemplary proximal portion of the needle system shown in FIG. 14. The exemplary needle is shown in an advanced or extended position, and the exemplary outer sheath is shown in an un-advanced or un-extended position.

FIG. 23 illustrates a partially cross-sectional side view of an exemplary proximal portion of the needle system shown in FIG. 14. Both the exemplary needle and the exemplary outer sheath are shown in an advanced or extended position.

FIGS. 24 and 25 illustrate an exemplary needle system including multiple telescoping sections in accordance with an embodiment of the present disclosure. FIG. 24 illustrates the needle system in an extended configuration, and FIG. 25 illustrates the needle system in a retracted configuration.

Figure 26:
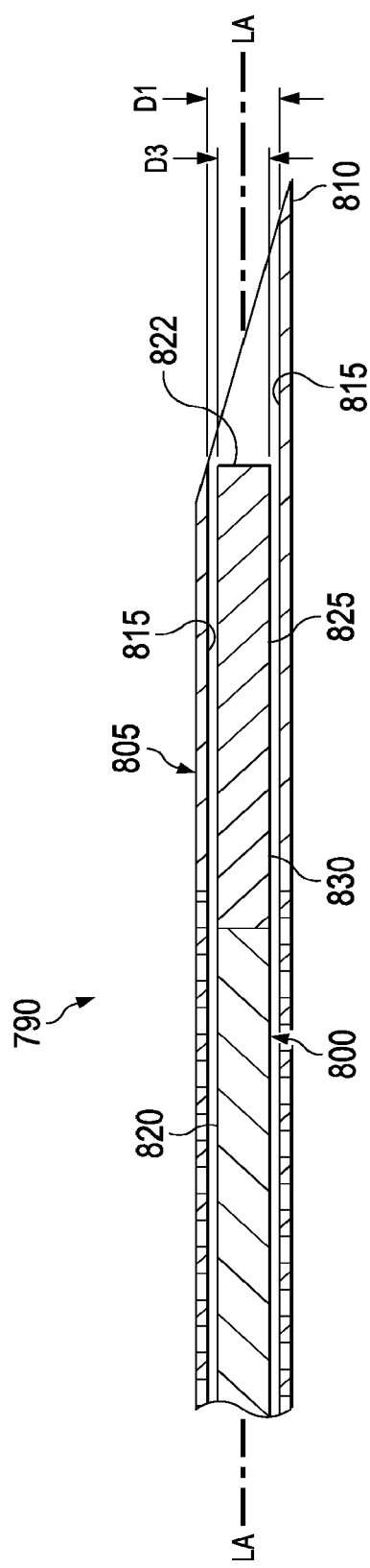

FIG. 26 illustrates an exemplary sensor stylet positioned within an exemplary medical instrument according to one embodiment of the present disclosure.

Figure 27:
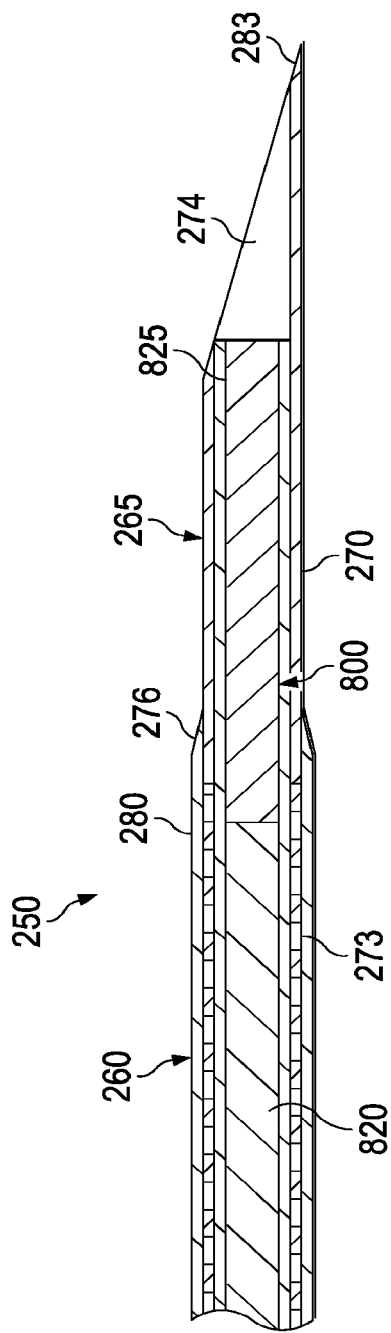

FIG. 27 illustrates the sensor stylet shown in FIG. 26 positioned within the exemplary needle system shown in FIGS. 3A-3C.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates.

In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an elongated object.

It will be appreciated that the terms "proximal" and "distal" are used herein with reference to a clinician manipulating an end of an instrument extending from the clinician to a surgical site. The term "proximal" refers to the portion of the instrument closer to the clinician, and the term "distal" refers to the portion of the instrument further away from the clinician and closer to the surgical site. For conciseness and clarity, spatial terms such as "horizontal," "vertical," "above," and "below" may be used herein with respect to the drawings. However, surgical instruments are used in many orientations and positions, and there terms are not intended to be limiting and absolute.

The present disclosure relates generally to steerable, flexible needle systems used in minimally invasive medical procedures, including without limitation diagnostic, surgical, and/or therapeutic procedures. In some instances, embodiments of the present disclosure are configured to be part of a teleoperational system. Those of skill in the art will realize that the steerable, flexible needle systems disclosed herein may be utilized in similar (e.g., non-teleoperational) applications requiring a steerable, flexible needle.

The needle systems disclosed herein comprise an outer sheath and a flexible needle. The flexible needles and outer sheaths disclosed herein are arranged in a telescoping fashion to allow the outer sheath to advance distally and surround the needle as or after it advances into tissue. In one aspect, the needle systems disclosed herein are configured to include position/shape sensors that extend axially along the steerable length of the needle and terminate close to the needle tip. The outer sheaths disclosed herein may minimize the bending strain on the sensors as well as protect the needle during insertion and progression through anatomical tissue. These features of the needle systems disclosed herein may enhance the steerability, stability, and distance/trajectory control of a needle during insertion in a minimally invasive procedure. Thus, the needle systems disclosed herein may improve the performance of steerable needles, and may increase the range of suitable applications for steerable needles. For example, in one instance, the flexible needle systems disclosed herein may enable the user to more accurately reach and sample a target biopsy location, more easily navigate around critical structures, and decrease the chance of inaccurate biopsies.

Figure 1:
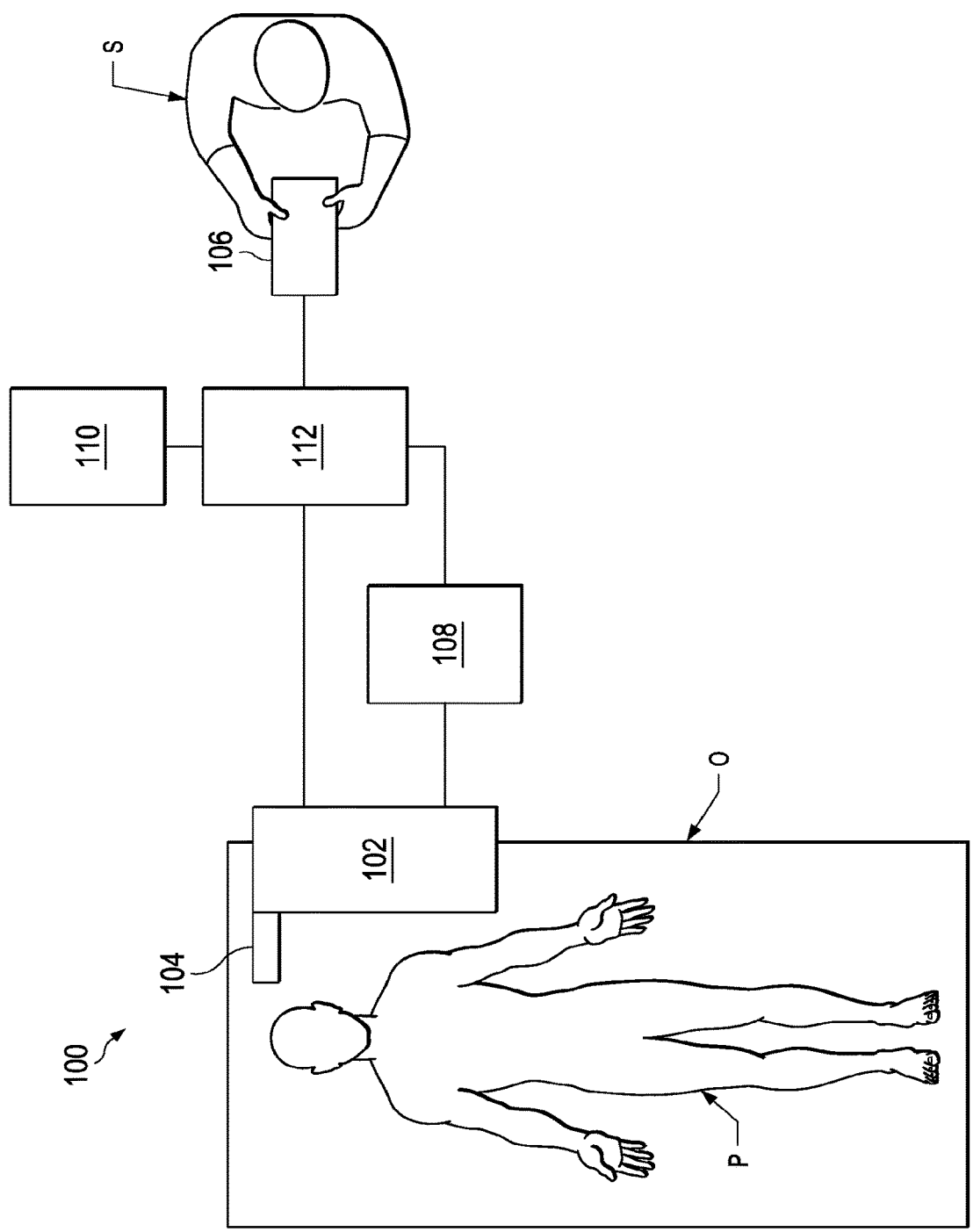
FIG. 1 illustrates a teleoperational medical system in accordance with an embodiment of the present disclosure.

According to various embodiments, medical procedures, such as biopsy procedures, may be performed using a teleoperational system to guide instrument delivery. Referring to FIG. 1 of the drawings, a teleoperational medical system for use in, for example, medical procedures including diagnostic, therapeutic, or surgical procedures, is generally indicated by the reference numeral 100. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1, the teleoperational medical system 100 generally includes a teleoperational assembly 102 mounted to or near an operating table O on which a patient P is positioned. A medical instrument system 104 is operably coupled to the teleoperational assembly 102. An operator input system 106 allows a surgeon or other type of clinician S to view images of or representing the surgical site and to control the operation of the medical instrument system 104.

The operator input system 106 may be located at a surgeon's console, which is usually located in the same room as operating table O. It should be understood, however, that the surgeon S can be located in a different room or a completely different building from the patient P. Operator input system 106 generally includes one or more control device(s) for controlling the medical instrument system 104. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and 10 which may also include an actuatable handle for actuating instruments (for example, for closing grasping jaws, applying an electrical potential to an electrode, delivering a medicinal treatment, and the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of motors that drive inputs on the medical instrument system 104. These motors move in response to commands from the control system (e.g., a control system 112). The motors include drive systems which when coupled to the medical instrument system 104 20 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes a sensor system 108 with one or more sub-systems for receiving information about the instruments of the teleoperational assembly. Such sub-systems may include a position sensor system (e.g., an electromagnetic 30 (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

Alternatively or additionally, display system 110 may present images of the surgical site recorded and/or imaged preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and the like. The presented 10 preoperative or intra-operative images may include two-dimensional, three-dimensional, or four-dimensional (including e.g., time based or velocity based information) images and associated image data sets for reproducing the images.

In some embodiments, the display system 110 may display a virtual visualization image in which the actual location of the medical instrument is registered (e.g., dynamically referenced) with preoperative or concurrent images to present the surgeon with a virtual image of the internal surgical site at the location of the tip of the medical instrument.

In other embodiments, the display system 110 may display a virtual visualization image in which the actual location of the medical instrument is registered with prior images (including preoperatively recorded images) or concurrent images to present the surgeon with a virtual image of a medical instrument at the surgical site. An image of a portion of the medical instrument system 104 may be superimposed on the virtual image to assist the surgeon controlling the medical instrument.

The teleoperational medical system 100 also includes a control system 112. The control system 112 includes at least one memory and at least one processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104. Virtual navigation using the virtual visualization system is based upon reference to an acquired dataset associated with the three dimensional structure of the anatomical passageways. More specifically, the virtual visualization system processes images of the surgical site imaged using imaging technology 20 such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intra-operatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomical Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
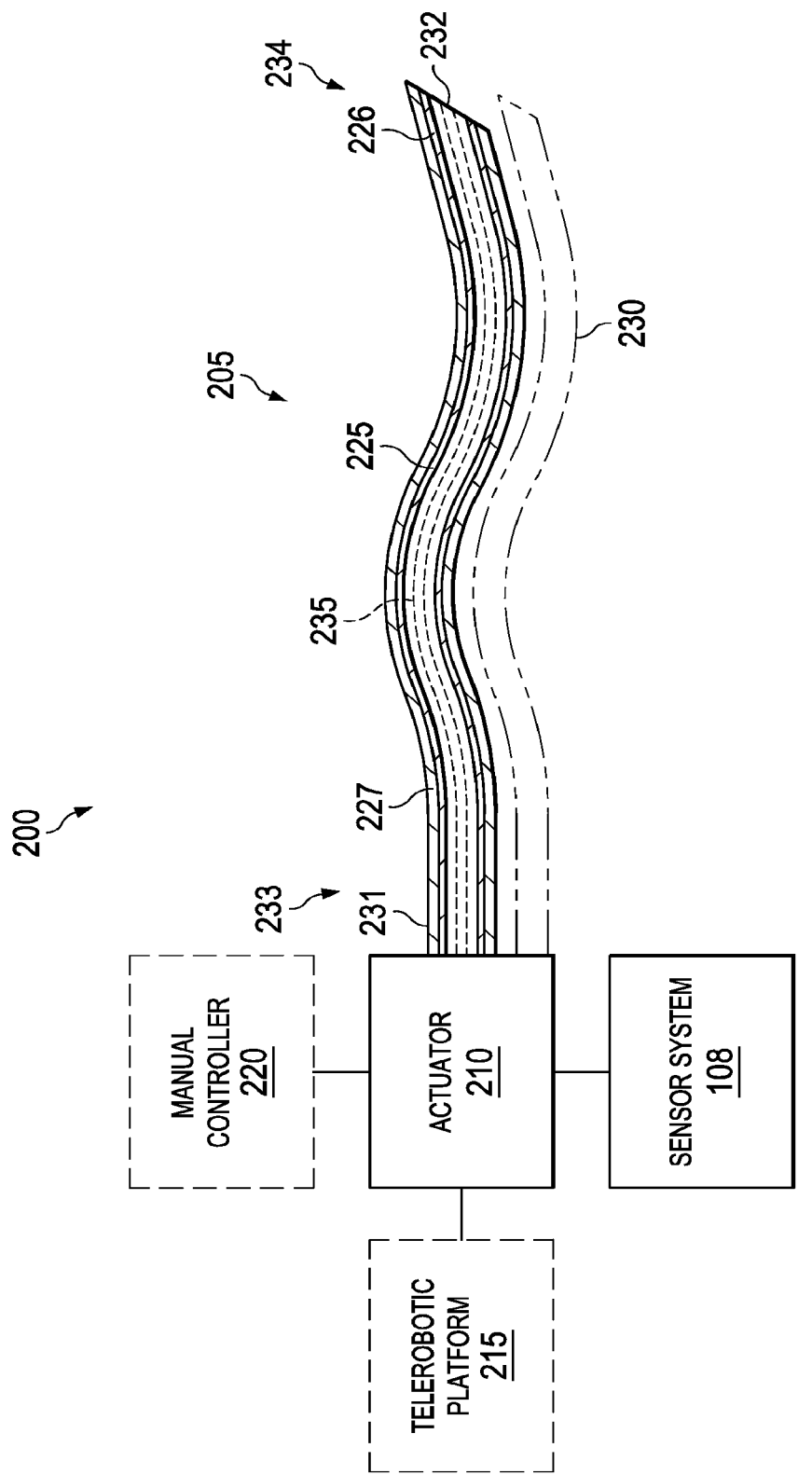
FIG. 2 illustrates a block diagram of a medical system including an exemplary needle system in accordance with an embodiment of the present disclosure.

FIG. 2 illustrates a medical instrument system 200 that includes an exemplary needle system 205, an actuator 210, and the sensor system 108. The needle system 205 may be the same as the medical instrument system 104 of the teleoperational medical system 100. In the pictured embodiment, the needle system 205 is manipulated (e.g., mechanically articulated or otherwise moved) by an actuator 210. In some embodiments, the actuator 210 may be controlled by a teleoperational platform 215 (e.g., the teleoperational platform 215 may send control signals to the actuator 210). The teleoperational platform 215 may include the teleoperational medical system 102 shown in FIG. 1. During the procedure, the teleoperational platform 215 may enable mechanical articulation and control of a variety of medical instruments in addition to the needle system 205, such as, by way of non-limiting example, tissue graspers, electrosurgical cautery probes, retractors, staplers, vessel sealers, endoscopes, scalpels, ultrasonic shears, and suction/irrigation instruments. In various embodiments, the medical instrument system 200 may include a flexible bronchial instrument, such as a bronchoscope or bronchial catheter for use in examination, diagnosis, biopsy, or treatment of a lung. The system is also suited for navigation and treatment of other tissues, via natural or surgically created connected passageways, in any of a variety of anatomical systems including the colon, the intestines, the kidneys, the brain, the heart, the circulatory system, or the like.

Alternatively, the medical instrument system 200 may be used for non-teleoperational exploratory procedures or in procedures involving traditional manually operated medical instruments, such as endoscopy. In such instances, the actuator 210 may be controlled manually by an optional manual controller 220. In some embodiments, the optional manual controller 220 is the actuator 210 itself (e.g., a knob, handle, or grip for a rotating needle). In other embodiments, the optional manual controller 220 can be a handle(s), trigger(s), lever(s), grip(s), or any other user interface for providing control inputs to the actuator 210. The optional manual controller 220 may be connected to the actuator 210 in a direct mechanical linkage and/or via electronic control, and may communicate with the actuator 210 in a wired and/or wireless fashion.

The needle system 205 includes an elongate instrument 225 including a rigid distal portion 226 and surrounded by an outer sheath 227. In the pictured embodiment, the elongate instrument 225 comprises a steerable, flexible needle including a rigid needle tip (described in further detail below with relation to FIG. 13). In other embodiments, the needle system 205 includes another type of elongate instrument instead of a needle. The needle system 205 can be manipulated by the actuator 210. In various embodiments, the needle system 205 can include any number of steerable, flexible needles, as indicated by optional needle 230 (along with any actuation, control, sensing, and/or processing elements required for the additional needles). In one example, the actuator 210 can manipulate the needle 225 by steering the needle 225 along a desired surgical trajectory to a target location within the patient, changing the shape of the needle 225, and/or changing the orientation of the needle 225.

As used herein, steerable needles refer to a broad category of flexible needles with control inputs at the base (i.e., outside the body of the patient) and distal regions meant for piercing or puncturing target tissue. Depending on the shape and mechanical properties of the needle, interaction forces between the needle and the patient anatomy (i.e., the target tissue and/or any intervening anatomy between the surgical entry point and the target tissue) can cause the needle to deflect, such that steering can be provided by simply applying rotation to the base of the needle. Alternatively or additionally, a steerable needle can include active actuators (e.g., the actuator 210) to provide shaping and directionality. Steerable needles generally have a sufficiently high axial stiffness and a tip shape to allow them to puncture or penetrate tissue with minimal axial compression, as compared to catheter-type devices that have a low axial stiffness and are not suited to penetrate or puncture.

Note that the term "flexible" in association with a steerable needle should be broadly construed. In essence, it means the needle can be bent without harm. For example, a flexible steerable needle may include a series of closely spaced components that are similar to "vertebrae" in a snake-like arrangement. In such an arrangement, each component is a short link in a kinematic chain, and movable mechanical constraints (e.g., pin hinge, cup and ball, 5 and the like) between each link may allow one (e.g., pitch) or two (e.g., pitch and yaw) degrees of freedom (DOF) of relative movement between the links. As another example, a flexible steerable needle may be continuous, such as a closed bendable tube (e.g., nitinol, polymer, and the like) or other bendable piece (e.g., kerf-cut tube, helical coil, and the like).

The needle system 205 includes a proximal end 231 and a distal end 232. The needle system 205 has an outer diameter ranging from 0.5 mm to 3.0 mm. For example, in one embodiment, the needle system 205 has an approximately 1.5 mm outer diameter. Other needle system outer diameters may be larger or smaller. In some embodiments, the needle system outer diameter tapers from the proximal end 231 to the distal end 232. In other embodiments, the needle system outer diameter at the proximal end 232 is greater than the needle system outer diameter at the distal end 232. In some embodiments, the needle system outer diameter is substantially unchanged throughout the length of the needle 225. In alternative embodiments, the needle system outer diameter tapers throughout the length of the needle 225. In other embodiments, there can be an abrupt change or stop in needle system 205 between a larger outer diameter of a proximal portion 233 to a smaller diameter of a distal portion 234 of the needle system 205. The above dimensions are provided for exemplary purposes only, and are not intended to be limiting. Other dimensions are contemplated.

In the pictured embodiment, the needle system 205 further includes a sensor system 235. The sensor system 235 is substantially aligned with at least a portion of the needle 225. If the needle system 205 is the medical instrument system 104 of the teleoperational medical system 100 shown in FIG. 1, the sensor system 235 may be a component of the sensor system 108. If the needle system 205 is manually operated or otherwise used for non-robotic procedures, the sensor system 235 may be coupled to a tracking system that interrogates the shape sensor and processes the received shape data. Regardless of the specific steering 3 0 mechanism of the needle 225, the usability of the needle system 205 is enhanced by the inclusion of the sensor system 235. The sensor system 235 can determine the position, orientation, speed, pose, and/or shape of the distal end 232 and/or of one or more discrete segments along the needle 225. The data read by the sensor system 235 is converted into useable shape and/or positional information by the sensor system 108 and/or the control system 112 shown in FIG. 1. The shape and/or positional information can then be used to guide further manipulation of the needle 225.

In the pictured embodiment, the sensor system 235 is a sensor that provides shape and/or position measurements of the needle 225. In the pictured embodiment, the sensor system 235 comprises an EM sensor system that can be used for point localization (i.e., position/orientation measurement). In some embodiments, the sensor system 235 includes multiple EM sensors or a single EM sensor cumulatively measured at various time intervals to determine the shape of the needle 225 at any given point in time. The EM sensor system 235 may include one or more conductive coils that may be subjected to an externally generated electromagnetic field. Each coil of the EM sensor system 235 then produces an induced electrical signal having characteristics that depend on the position and orientation of the coil relative to the externally generated electromagnetic field. In one embodiment, the EM sensor system may be configured and positioned to measure six degrees of freedom ("6-DOF"), e.g., three position coordinates X, Y, Z and three orientation angles indicating pitch embodiment, the EM sensor system may be configured and positioned to measure five degrees of freedom ("5-DOF"), e.g., three position coordinates X, Y, Z and two orientations of a base point. For example, in some embodiments, the sensor system 235 comprises a 5-DOF EM sensor configured to provide position and/or orientation data related to the tip of the needle (e.g., to allow the user to recognize where the needle tip is within the patient as the needle is extended). Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

In some embodiments, the sensor system 235 may include an optical fiber aligned with the flexible needle 225 (e.g., the optical fiber may be provided within an interior sensor lumen 550 as shown in FIG. 16). The optical fiber of the sensor system 235 may form a fiber optic bend sensor for determining the shape of at least a portion of the needle system 205. Various systems and methods for monitoring the shape and relative position of an optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the needle system 205 may be determined using other techniques.

More specifically, light passing through the optical fiber is processed to detect the shape of the needle system 205 and for utilizing that information to assist in medical procedures. The sensor system (e.g. sensor system 108 or another type of tracking system as described in FIG. 3) may include an interrogation system for generating and detecting the light used for determining the shape of the needle system 205. This information, in turn, can be used to determine other related variables, such as velocity and acceleration of the parts of an medical instrument.

The sensor system 235 may include a single continuous sensing region over the length of the needle system 205 or multiple sensing regions distributed along the length of the needle system 205. In other embodiments, the sensor system 235 comprises an elongate sensor that provides shape measurements along the length of the needle 225. In contrast to a discrete position sensor, an elongate sensor enables shape measurements along the length of the needle 225 with a single sensor. The integrated nature of a single elongate shape sensor provides more accurate shape measurement of the needle 225, which enables more precise control and/or enhanced error correction to ensure that the needle 225 accurately traverses a desired surgical trajectory.

Note that although the sensor system 235 is depicted and described as a single elongate sensor for explanatory purposes, in other embodiments the sensor system 235 can include multiple discrete shape sensors. In one such embodiment, each shape sensor may measure the shape of a continuous portion of the overall length of the needle 225. Multiple shape sensors may provide greater shape modeling accuracy or may be useful in compensating for environmental factors that can affect the sensors (e.g., temperature variations along the length of the needle 225).

The needle system 205 may also house cables, linkages, or other steering controls (not shown in FIG. 2) that extend between the actuator 210 and the distal end 232 to controllably bend or turn the proximal portion 233 and/or the distal portion 234 of the needle 225. In some embodiments, the needle 225 can define one or more additional lumens through which other medical instruments, cables, linkages, and/or other steering controls may extend.

In embodiments in which the instrument system 200 is actuated by a teleoperational assembly, the actuator 210 may include drive inputs that couple to motorized drive elements of the teleoperational assembly. In embodiments in which the instrument system 200 is manually operated, the actuator 210 may include gripping features, manual actuators, and other components for manually controlling the motion of the instrument system. In some embodiments, the proximal portion 233 is configured to passively deflect in response to forces acting upon the flexible body, and the distal portion 234 is configured to actively articulate in response to the teleoperational assembly and/or control signals from the actuator 210.

FIGS. 3A-3C illustrate side views of an exemplary steerable, flexible needle system 250 in accordance with an embodiment of the present disclosure. In particular, FIGS. 3A-3C illustrate a distal portion 255 of the needle system 250. The needle system 250 may be the same as the needle system 205 described above in relation to FIG. 2. In the pictured embodiment, the distal portion 255 of the needle system 250 includes an outer sheath 260, which may be the same as the outer sheath 227 described above in relation to FIG. 2.

FIG. 3A illustrates a needle 265 positioned within the outer sheath 260 in a partially extended condition. As shown in FIG. 3A, the outer sheath 260 comprises a generally cylindrical, hollow tube at least partially surrounding the needle 265. The needle 265 has a rigid distal section 270 (e.g, the needle 265 may be the same as the needle 225 described above in relation to FIG. 2). The needle 265 is shaped and sized to be slidably received within a lumen 272 of the outer sheath 260. In some embodiments, the needle 265 has varying degrees of flexibility along its length. For example, in the pictured embodiment, the needle 265 includes a flexible proximal section 273 that is significantly more flexible than the rigid distal section 270. In some embodiments, the flexible proximal section 273 comprises a coiled hollow tube. The flexible proximal section 273 and the rigid distal section 270 share a common needle lumen 274.

In some embodiments, the outer sheath 260 has varying degrees of flexibility along its length. In the pictured embodiment, the outer sheath 260 comprises a flexible proximal portion 275 and a rigid distal portion 280. In some embodiments, the flexible proximal portion 275 and the rigid distal portion 280 have varying degrees of flexibility and/or steerability along its length. In the pictured embodiment, both the rigid distal portion 280 of the outer sheath 260 and the rigid distal section 270 of the needle 265 are significantly less 30 flexible than the flexible proximal portion 275 of the outer sheath 260. As shown, the needle 265 can extend distally from a distal end 276 of the outer sheath 260. In particular, both the flexible proximal section 273 and the rigid distal section 270 can extend distally from the distal end 276 of the outer sheath 260 (for example, as described further in FIG. 3C.

The flexible proximal portion 275 and the rigid distal portion 280 are fixedly attached to one another by any of a variety of known methods, including by way of non-limiting example, adhesive, welding (e.g., laser-welding), and/or mechanical fasteners. For example, in the pictured embodiment, a distal end 281 of the flexible proximal portion 275 is attached to a proximal end 282 of the rigid distal portion 280 by laser-welding. In some embodiments, however, the flexible proximal portion 275 can extend over the rigid distal portion 280 and attach to the rigid distal portion 280 at a more distal location along the length of the rigid distal portion 280. In some embodiments, the rigid distal portion 280 is an integral extension of the flexible proximal portion 275.

In FIG. 3B, the needle 265 is shown in a non-extended condition where the rigid distal section 270 of the needle 265 (i.e., a needle tip of the needle 265) is positioned entirely within the distal rigid portion 270 of the outer sheath 260, and a distal end or needle tip 283 of the needle 265 is positioned proximal to the distal end 276 of the outer sheath 260. In particular, the needle tip 283 is positioned entirely within the rigid distal portion 280 of the outer sheath 260. In the pictured embodiment, when the needle 265 is completely sheathed within the outer sheath 260 with the rigid distal section 270 within the rigid distal portion 280, the rigid distal portion 280 of the outer sheath 260 forms a rigid section or rigid tube section 284 of the needle system 250 having a length Lr. The remainder of the outer sheath 260 (i.e., the flexible proximal portion 275) forms a flexible section 285 of the needle system 300.

By telescoping the needle tip 283 into the rigid section 284 as shown in FIG. 3B, the overall length Lr of the rigid section 284 of the distal portion 255 of the needle system 250 is decreased as compared to a needle system having a non-telescoping needle tip. As shown in FIG. 3A, when the rigid distal section 270 is extended outside the rigid distal portion 280 of the outer sheath 260, the length Lr of the rigid section 284 comprises the length of the rigid distal portion 280 of the outer sheath 260 and the length of the rigid distal section 270 of the needle 265. When the rigid distal section 270 of the needle 265 is extended outside the outer sheath 260, the length Lr of the rigid section 284 may range from 10 mm-20 mm. As shown in FIG. 3B, when the rigid distal section 270 is sheathed within the outer sheath 260, the length Lr of the rigid section 284 comprises a length Ld of the rigid distal portion 280 of the outer sheath 260. Thus, when the rigid distal section 270 of the needle 265 is sheathed 3 0 within the outer sheath 260, the length Lr of the rigid section 284 may range from 5 mm-10 mm. For example, in one embodiment, the length Lr measures 8 mm when the rigid distal section 270 is sheathed within the outer sheath 260. The above dimensions are provided for exemplary purposes only, and are not intended to be limiting. Other dimensions are contemplated.

In FIG. 3C, the needle 265 is shown in an extended condition where the distal end 283 of the needle 265 is positioned further distal to the distal end 276 of the sheath tip 325 than shown in FIG. 3A. In the pictured embodiment, the distal end 283 is shaped as a beveled, sharpened tip (e.g., a Baker needle tip). In alternative embodiments, the distal end design of 5 the needle 265 can take any form or shape as required for the particular procedural requirements of the medical procedure (e.g., a rounded tip such as a Tuohy needle tip or a solid tip such as a Sprotte needle tip). Various other needle tip designs will be readily apparent to one of skill in the art. The flexible proximal section 273 and the rigid distal section 270 are fixedly attached to one another by any of a variety of known methods, including by way of non-limiting example, adhesive, welding (e.g., laser-welding), and/or mechanical fasteners. For example, in the pictured embodiment, the flexible proximal section 273 is attached to the rigid distal section 270 by laser-welding.

The rigid distal portion 280 of the sheath 260 includes the length Ld that may range from 7 mm-9 mm. For example, in one embodiment, the length Ld measures 8 mm. The rigid distal section 270 of the needle 265 includes a length Ln that may range from 7 mm-9 mm. For example, in one embodiment, the length Ln measures 8 mm. The length Ln of the rigid distal section 270 is equal to or less than the length Ld of the rigid distal portion 280 shown in FIG. 3C. The above dimensions are provided for exemplary purposes only, and are not intended to be limiting. Other dimensions are contemplated. The length Ln represents a 20 length of distal rigid section 286 at the distal end of the needle system 250.

In FIG. 3C, the length Lf represents the length of a distal flexible section 287 of the needle system 250 when the needle 265 is in a fully extended position. In particular, the flexible proximal section 273 of the needle 265 forms the distal flexible section 287 when the flexible proximal section 273 is extended distally past the distal end 276 of the outer sheath 25 260. The length Lf may range from 10 mm-15 mm. In one embodiment, the length Lf is 15 mm. The more proximal rigid section 284 includes the rigid tube portion 280 of the outer sheath 260, and the more proximal flexible section 285 includes the flexible proximal portion 275 of the outer sheath 260. A length Lt represents the total length of the rigid section 284, the flexible section 287, and the rigid section 286 (i.e., when the needle 265 is in a fully 30 extended condition). The length Lt may range from 20 mm to 45 mm. For example, in one embodiment, the length Lt measures 30 mm. The above dimensions are provided for exemplary purposes only, and are not intended to be limiting. Other dimensions are contemplated.

FIG. 4 illustrates a side view of an exemplary steerable, flexible needle system 300 in accordance with an embodiment of the present disclosure. In particular, FIG. 4 illustrates a distal portion 305 of the needle system 300. The needle system 300 may be the same as the needle system 205 described above in relation to FIG. 2. In the pictured embodiment, the distal portion 305 of the needle system 300 includes an outer sheath 310, which may be the same as the outer sheath 227 described above in relation to FIG. 2.

As shown in FIG. 4, the outer sheath 310 comprises a generally cylindrical, hollow tube configured to at least partially surround a needle (e.g, the needle 225 described above in relation to FIG. 2 and/or the needle 500 as described in further detail below with reference to FIG. 14) during a minimally invasive procedure. In some embodiments, the outer sheath 310 has varying degrees of flexibility along its length. In the pictured embodiment, the outer sheath 310 comprises a sheath element 315, an elongate tube 320, and a sheath tip 325. In some embodiments, the sheath element 315, the elongate tube 320, and a sheath tip 325 have varying degrees of flexibility and/or steerability. For example, in one aspect, the sheath tip 325 is significantly less flexible than the elongate tube 320 and the sheath element 315. With respect to FIGS. 4-24, the sheath element 315 and the elongate tube 320 together may correspond to the flexible proximal portion 275 of the outer sheath 260 shown in FIG. 3A, and the sheath tip 325 may correspond to the rigid distal portion 280 shown in FIG. 3A, and the following descriptions may apply to the embodiment shown in FIGS. 3A-3C.

FIG. 5 is a diagrammatic illustration of a side view of the outer sheath 310 shown in FIG. 4. The sheath element 315 has a length L1 extending from a proximal end 330 to a distal end 335. The length L1 of the sheath element 315 may range from 20 inches to 50 inches. For example, in one embodiment, the sheath element 315 has a length L1 of 40 inches (101.6 cm). The elongate tube 320 has a length L2 extending from a proximal end 340 to a distal end 345. The length L2 of the elongate tube 320 may range from 0.1 inches to 3.0 inches. For example, in one embodiment, the elongate tube 320 has a length L2 of 0.90 inches (2.286 cm). The sheath tip 325 has a length L3 extending from a proximal end 350 to a distal end 355. The length L3 of the sheath tip 325 may range from 0.02 inches to 0.2 inches. For example, in one embodiment, the sheath tip 325 has a length L3 of 0.10 inches (0.254 cm). The above dimensions are provided for exemplary purposes only, and are not intended to be limiting. Other dimensions are contemplated.

The sheath element 315 and the elongate tube 320 are fixedly attached to one another by any of a variety of known methods, including by way of non-limiting example, adhesive, welding (e.g., laser-welding), and/or mechanical fasteners. For example, in the pictured embodiment, the distal end 335 of the sheath element 315 is attached to the proximal end 340 of the elongate tube 320 by laser-welding. In some embodiments, however, the sheath element 315 can extend over the elongate tube 320 and attach to the elongate tube 320 at a more distal location along the length of the elongate tube 320. In some embodiments, the elongate tube 320 is an integral extension of the sheath element 315.

The sheath tip 325 and the elongate tube 320 are fixedly attached to one another by any of a variety of known methods, including by way of non-limiting example, adhesive, welding (e.g., laser-welding), and/or mechanical fasteners. For example, in the pictured embodiment, the proximal end 350 of the sheath tip 325 is attached to the distal end 345 of the elongate tube 320 by laser-welding. In some embodiments, the sheath tip 325 is an integral extension of the elongate tube 320.

FIG. 6 is a diagrammatic illustration of a cross-sectional view of the needle 300 through the line 6-6 shown in FIG. 5. In the pictured embodiment, the outer sheath 310 has an outer diameter that varies along its length. In particular, the outer sheath 310 tapers slightly from the sheath element 315 to the distal end 355 of the sheath tip 325. In other embodiments, the outer sheath 310 has a substantially uniform outer diameter from the sheath element 315 to the sheath tip 325. The sheath element 315 has an outer diameter DI ranging from 0.035 inches to 0.10 inches. For example, in one embodiment, the sheath element 315 has an outer diameter DI of 0.07 inches (0.178 cm). The sheath element 315 has an inner diameter D2 ranging from 0.025 inches to 0.075 inches. For example, in one embodiment, the sheath element 315 has an inner diameter D2 of 0.054 inches (0.137 cm). The elongate tube 320 has an outer diameter D3 ranging from 0.036 inches to 0.065 inches. For example, in one embodiment, the elongate tube 320 has an outer diameter D3 of 0.059 inches (0.15 cm). The sheath tip 325 has an outer diameter D4 ranging from 0.036 inches to 0.065 inches. For example, in one embodiment, the sheath tip 325 has an outer diameter D4 of 0.059 inches (0.15 cm). As described further below in relation to FIG. 12, in the pictured embodiment, the sheath tip 325 tapers toward the distal end 355. In other embodiments, the sheath tip 325 does not taper. The above dimensions are provided for exemplary purposes only, and are not intended to be limiting. Other dimensions are contemplated.

FIG. 7 illustrates a diagrammatic side view of the sheath element 315. In the pictured embodiment, the sheath element 315 comprises a flexible length of material wound into a spiral or coiled configuration to form resiliently flexible tubular body 360. In some embodiments, the sheath element 315 is configured to be bendable as well as compressible. In other embodiments, the sheath element 315 may comprise any type of flexible tube or flexible sheath, including, by way of non-limiting example, a continuous, solid-walled elastomeric tube. In the pictured embodiment, each helical turn 362 of the material has a length L4 ranging from 0.006 inches to 0.06 inches. For example, in one embodiment, the helical turn 362 has a length L4 of 0.020 inches. The above dimensions are provided for exemplary purposes only, and are not intended to be limiting. Other dimensions are contemplated.

FIG. 8 illustrates a diagrammatic cross-sectional view of the sheath element 315 through the line 8-8 shown in FIG. 7. In particular, FIG. 7 illustrates a diagrammatic view of a single helical turn 362 of the sheath element 315. The body 360 of the sheath element 315 defines a lumen 365. The body 360 of the sheath element 315 has a wall thickness T1 extending from an inner luminal surface 370 to an outer surface 375. The wall thickness T1 of the sheath element 315 is configured to be as thin as practicable so as to enable the sheath element 315 to penetrate and curve within the patient's tissue while still being sufficiently strong to protect and guide the needle housed within the sheath coil (e.g., the needle 500 as described further below in relation to FIG. 14). The wall thickness T1 may range from 0.004 15 inches to 0.016 inches. For example, in one embodiment, the wall thickness T1 is 0.008 inches (0.02 cm). The above dimensions are provided for exemplary purposes only, and are not intended to be limiting. Other dimensions are contemplated.

In the pictured embodiment, the sheath element 315 comprises a flexible coil formed of stainless steel. In various embodiments, the sheath element 315 may be made of any suitable biocompatible material that provides the requisite tensile and flexural properties. Suitable materials may include, by way of non-limiting example, shape memory material such as Nitinol, stainless steel, and plastics. In some embodiments, the sheath element 315 is made from the same material throughout (e.g., stainless steel from the proximal end 330 to the distal end 335). In other embodiments, the sheath element 315 may be made from two or 25 more different materials (e.g., stainless steel in a less flexible zone and Nitinol in a more flexible zone).

In some embodiments, a flexible jacket 379 may surround the sheath element 315. The flexible jacket 379 may provide additional resistance to stretching of the sheath element 315 as the needle 300 curves or bends. In some embodiments, the flexible jacket is formed of 3 0 plastic. In other embodiments, the flexible jacket 379 may be formed of any suitable biocompatible material that provides the requisite tensile and flexural properties.

FIG. 9 illustrates a diagrammatic side view of the elongate tube 320, and FIG. 10 illustrates a diagrammatic side view of an enlarged portion 380 of the elongate tube 320. The elongate tube 320 comprises a discrete portion of the outer sheath 310 disposed between the sheath element 315 and the sheath tip 325. The elongate tube 320 defines a lumen 382. The elongate tube 320 provides an increased resistance to buckling as the needle system 300 is advanced into tissue. In some embodiments, the elongate tube 320 is less likely to buckle than the sheath element 315.

The elongate tube 320 includes a plurality of slots 385. The slots 385 extend from an inner surface 386 (as shown in FIG. 14) of the elongate tube 320 to an outer surface 387 (as shown in FIG. 14) of the elongate tube. The slots 385 are formed with a pattern that balances axial, bending, and torsional stiffness. In the pictured embodiment, the slots 385 are formed substantially perpendicular to a longitudinal axis AA and extend approximately 170 degrees around the circumference of the elongate tube 320. In the pictured embodiment, the slots 385 alternate with respect to their circumferential position on the elongate tube 320. The slots 385 allow the elongate tube 320 to bend in multiple dimensions. In some embodiments, the slots 385 are laser-cut. In some embodiments, the frequency and pattern of cuts in any given portion of the elongate tube 320 may determine the flexibility of that portion. The elongate tube 320 may bend or curve until a slot sidewall 387a abuts an adjacent slot sidewall 387b (shown in FIG. 10) and prevents further bending of the elongate tube 320. In some embodiments, a higher spatial frequency of cuts may correspond to a higher flexibility. The slots 385 illustrated in the drawings are merely exemplary, and are not intended to be limiting in number, type, arrangement, or shape. In various embodiments, the elongate tube 320 may have any number, type, shape, and arrangement of slots 385.

As shown in FIGS. 9 and 10 each slot 385 includes a width WI. The width WI may range from 0.001 inches to 0.005 inches. For example, in one embodiment, the width WI of each of the slots 385 is uniform and measures 0.002 inches (0.005 cm). In some embodiments, the widths of different slots vary. In the pictured embodiment, a length L6 between each slot 385 is uniform and measures 0.020 inches (0.051 cm). In other embodiments, the length L6 between different adjacent slots can vary.

In the pictured embodiment, the slots 385 only extend along a portion of length of the elongate tube 320. As shown in FIG. 9, the elongate tube 320 includes a rigid tube portion 390 lacking slots and having a length L5. The rigid tube portion 390 may be less flexible than a flexible tube portion 395 of the elongate tube 320 (i.e., the portion including the plurality of slots 385). In some embodiments, the rigid tube portion 390 comprises a rigid length of the same material as the elongate tube 320. The length L5 of the rigid tube portion 390 of the elongate tube 320 may range from 0.1 inches to 0.5 inches. For example, in one embodiment, the rigid tube portion 390 of the elongate tube 320 has a length L5 of 0.27 inches (7 mm). In other embodiments, the slots may extend the entire length (e.g., the length L2) of the elongate tube 320, or along a different portion of the elongate tube 320.

In the pictured embodiment, the elongate tube 320 comprises a partially flexible hypotube formed of stainless steel. In various embodiments, the elongate tube 320 may be made of any suitable biocompatible material that provides the requisite tensile and flexural properties. Suitable materials may include, by way of non-limiting example, shape memory material such as Nitinol, stainless steel, and plastics. In some embodiments, the elongate tube 320 is made from the same material throughout (e.g., Nitinol from the proximal end 340 to the distal end 345). In other embodiments, the elongate tube 320 may be made from two or more different materials (e.g., stainless steel in a less flexible zone and Nitinol in a more flexible zone).

In some embodiments, a flexible jacket 391 may surround the elongate tube 320. The flexible jacket 391 may provide additional resistance to stretching of the elongate tube 320 as the needle 300 curves or bends. In some embodiments, the flexible jacket 391 is formed of plastic. In other embodiments, the flexible jacket 391 may be formed of any suitable biocompatible material that provides the requisite tensile and flexural properties. In some embodiments, the flexible jacket 391 is the same as the flexible jacket 379 that surrounds the sheath element 315 (shown in FIG. 8). In some embodiments, the flexible jacket 391 extends over the entire length L2 of the elongate tube 320. In other embodiments, the flexible jacket 20 391 extends over only a portion of the length of the elongate tube 320.

One technique for the construction of the elongate tube 320 is laser cutting technology, which may produce the elongate tube 320 in an automatic fashion (e.g., by computer numeric controlled cutting). Fine changes in the dimensions of the elongate tube 320 may be automatically programmed and generated using laser cutting technology. Other suitable manufacturing methods may include, by way of non-limiting example, water jet cutting, electrochemical etching, electrical discharge machining, and diamond cutting. In some embodiments, the creation of the slots 385 is followed by a suitable surface treatment, such as, by way of non-limiting example, etching or electro-polishing to deburr irregular surfaces or blunt sharp edges.

FIG. 11 illustrates a diagrammatic side view of the sheath tip 325. The sheath tip 325 comprises a discrete portion of the outer sheath 310 disposed distal to the elongate tube 320. The sheath tip 325 can protect the tip of the needle (e.g., the needle 225 shown in FIG. 2) as it is advanced into tissue. As illustrated in FIG. 11, the sheath tip 325 includes an outer diameter D4 at the proximal end 350 and an outer diameter D5 at the distal end 35 that is smaller than the outer diameter D4. In the pictured embodiment, the outer diameter of the sheath tip 325 tapers from a midsection 393 of the sheath tip 325 to the distal end 355. In other embodiments, the sheath tip 325 may not taper. In other embodiments, the sheath tip 325 may taper continuously from the proximal end 350 to the distal end 355.

The outer diameter D5 of the sheath tip 325 may range from 0.036 inches to 0.065 inches. For example, in one embodiment, the outer diameter D5 of the sheath tip 325 at the distal end 355 is 0.0445 inches (0.113 cm). The above dimensions are provided for exemplary purposes only, and are not intended to be limiting. Other dimensions are contemplated.

FIG. 12 illustrates a diagrammatic cross-sectional view of the sheath tip 325 along the line 12-12 shown in FIG. 11, and FIG. 13 illustrates a diagrammatic cross-sectional view of the sheath tip 325 at the midsection 393 along the line 13-13 shown in FIG. 11. As shown in FIG. 12, the sheath tip 325 comprises a hollow tubular body 395 defining a lumen 400. The body 395 includes a proximal portion 405, a distal portion 410, and a midportion 415 extending therebetween. The luminal diameter of the sheath tip 325 decreases from the proximal portion 405 to the distal portion 410. In particular, the proximal portion 405 includes an inner diameter D6, the distal portion 410 includes an inner diameter D7, and the inner diameter D7 is smaller than the inner diameter D6. The body 395 of the sheath tip 325 includes a wall thickness extending from a luminal inner surface 420 to an outer surface 425. In the pictured embodiment, the inner surface 420 slopes inward at an angle A1 to create a shoulder 430 within at the midportion 415 of the sheath tip 325.

In addition, the wall thickness of the sheath tip 325 increases from the proximal portion 405 to the distal portion 410, thereby allowing for the smooth and continuous outer surface 425 extending from the proximal end 350 to the distal end 355. In particular, the proximal portion 405 includes a wall thickness T2 extending from the inner surface 420 to the outer surface 425. The distal portion 410 includes a wall thickness T3 extending from the inner surface 420 to the outer surface 425. The wall thickness of the body 395 gradually increases from the wall thickness T2 to the wall thickness T3 through the midportion 415. In the pictured embodiment, the wall thickness T3 gradually decreases from the midsection 393 3 0 toward the distal end 355.

The inner diameter D6 of the sheath tip 325 may range from 0.025 inches to 0.075 inches. For example, in one embodiment, the inner diameter D6 of the sheath tip 325 is 0.0445 inches (0.113 cm). The inner diameter D7 of the sheath tip 325 may range from 0.02 inches to 0.08 inches. For example, in one embodiment, the inner diameter D7 of the sheath tip 325 is 0.0445 inches (0.113 cm). The above dimensions are provided for exemplary purposes only, and are not intended to be limiting. Other dimensions are contemplated.

The sheath tip 325 includes a length L3 (as shown in FIGS. 5 and 12), and the distal portion includes a length L6. The length L6 of the sheath tip 325 may range from 0.02 inches to 0.08 inches. For example, in one embodiment, the length L6 of the sheath tip measures 0.050 inches (0.127 cm). The above dimensions are provided for exemplary purposes only, and are not intended to be limiting. Other dimensions are contemplated.

The sheath tip 325 may be made of any suitable biocompatible material that provides the requisite tensile and flexural properties. Suitable materials may include, by way of non-limiting example, shape memory material such as Nitinol, stainless steel, and plastics. In some embodiments, the sheath tip 325 is made from the same material throughout (e.g., stainless steel from the proximal end 350 to the distal end 355). In other embodiments, the sheath tip 325 may be made from two or more different materials. In some embodiments, the sheath tip 325 may be coated with a biocompatible lubricant.

FIGS. 14 and 15 illustrate cross-sectional views of the exemplary steerable, flexible needle system 300 in accordance with an embodiment of the present disclosure. In particular, FIGS. 14 and 15 illustrate cross-sectional views of the distal portion 305 of the needle system 300. As shown in FIG. 14, the lumen 365 of the sheath coil, the lumen 382 of the elongate tube 320, and the lumen 400 of the sheath tip 325 are in communication with each other. Together, the lumen 365 of the sheath coil, the lumen 382 of the elongate tube 320, and the lumen 400 of the sheath tip 325 form the lumen 450 of the outer sheath 310. The needle system 300 includes a needle 500, which is slidably positioned within the lumen 450 of the outer sheath 310. The needle 500 and the outer sheath 310 are arranged in a telescoping fashion relative to each other. Thus, the needle 500 can extend distally from the outer sheath 310 (i.e., while the distal sheath 310 remains stationary). In some embodiments, the needle 500 and the outer sheath 310 can correspond to the needle 265 and the outer sheath 260 shown in FIG. 3A.

In some embodiments, the outer sheath 310 includes a mechanical stop element 502 to limit the distal extension of the needle 500 (i.e., from extending past the sheath tip 325 of the outer sheath 310). In the pictured embodiment, the mechanical stop element 502 is located within the lumen 450 and is configured to physically interface with the needle 500 to limit the distal movement of the needle. For example, in some embodiments, the needle 500 may include a mechanical stop element configured to interact with the mechanical stop element 502 to limit the distal advancement of the needle 500 within the outer sheath 310. In other embodiments, the mechanical stop element 502 may be located elsewhere on the needle system 300.

In FIG. 14, the needle 500 is depicted in a non-extended condition where the needle 500 is disposed entirely within the outer sheath 310. In FIG. 15, the needle 500 is depicted in an extended condition where the needle tip 505 of the needle 500 has partially emerged from the outer sheath 310.

The needle 500 includes a needle tip, distal section, or distal portion 505 and a needle jacket 510. In the pictured embodiment, the needle tip 505 comprises a hollow, rigid tube having a needle tip lumen 512 (as shown in FIG. 16) extending from a proximal end 515 to a distal end 520. In some embodiments, the needle tip 505 corresponds to the rigid distal section 270 of the needle 265 shown in FIGS. 3A-3C. In one embodiment, the needle 500 is a 22 gauge needle. The needle tip 505 is coupled to the needle jacket 510 at the proximal end 515. In the pictured embodiment, the needle tip 505 includes a plurality of apertures 525 adjacent the proximal end 515, and the needle jacket 510 couples to the apertures 525 (e.g., via extrusion into the needle tip lumen 512 and into the apertures 525). The apertures 525 and the features of the needle jacket 510 that couple to the apertures 525 (e.g., one or more extrusions into the needle tip lumen 512) are engagement features that together operate as a holding mechanism. In one aspect, the coupling of the apertures 525 with, e.g., one or more extrusions of the needle jacket 510 into the needle tip lumen 512, operate as a holding mechanism to maintain the needle tip 505 in an extended position relative to the needle jacket 510. In other embodiments, the needle tip 505 and the needle jacket 510 may be coupled in different way.

In FIG. 14, the needle 500 is shown in a non-extended condition where the needle tip 505 of the needle 500 (i.e., the rigid portion of the needle 500) is positioned entirely within the elongate tube 320 and the sheath tip 325, and the distal end 520 of the needle 500 is positioned proximal to the distal end 355 of the sheath tip 325. In particular, the needle tip 505 is positioned entirely within the rigid tube portion 390 of the elongate tube 320 and the sheath tip 325. When the needle tip 505 is sheathed or telescoped within the elongate tube 320 and the sheath tip 325, the rigid tube portion 390 of the elongate tube 320 and the sheath tip 325 together form a rigid section or rigid tube section 507 of the needle system 300. The remainder of the outer sheath 310 (i.e., the flexible tube portion 395 and the sheath element 315) form a flexible section 508 of the needle system 300.

By telescoping the needle tip into the rigid section 507 as shown in FIG. 14, an overall length L7 of the rigid section 507 of the distal portion 305 the needle system 300 is decreased as compared to a needle system having a non-telescoping needle tip. When the needle tip is sheathed within the outer sheath 310, the length L8 of the rigid section 507 comprises the length L5 of the rigid tube portion 390 of the elongate tube 320 in addition to the length L3 of the sheath tip 325. Thus, when the needle tip is sheathed within the outer sheath 310, the 5 length L7 of the rigid section 507 may range from 0.2 inches to 0.5 inches. For example, in one embodiment, the length L7 measures 0.35 inches (0.9 cm) when the needle tip 505 is sheathed within the outer sheath 310. The above dimensions are provided for exemplary purposes only, and are not intended to be limiting. Other dimensions are contemplated.

In FIG. 15, the needle 500 is shown in an extended condition where the distal end 520 of the needle 500 is positioned distal to the distal end 355 of the sheath tip 325. In the pictured embodiment, the distal end 520 of the needle tip 505 is shaped as a beveled, sharpened tip (e.g., a Baker needle tip). In alternative embodiments, the distal end design of the needle tip 505 can take any form or shape as required for the particular procedural requirements of the medical procedure (e.g., a rounded tip such as a Tuohy needle tip or a solid tip such as a Sprotte needle tip). Various other needle tip designs will be readily apparent to one of skill in the art.

The needle tip 505 includes an outer diameter D8. The outer diameter D8 of the needle tip 505 may range from 0.025 inches to 0.065 inches. For example, in one embodiment, the outer diameter D8 of the needle tip 505 is 0.042 inches (0.107 cm). In some embodiments, the outer diameter D8 of the needle tip 505 is configured to be slidably received within a catheter tool channel having a 2.1 mm diameter with a minimum centerline bend radius of 11.5 mm. The needle tip 505 includes a length LN that may range from 0.20 inches to 0.50 inches. For example, in one embodiment, the length LN measures 0.36 in (0.914 cm). The above dimensions are provided for exemplary purposes only, and are not intended to be limiting. Other dimensions are contemplated.

As depicted in FIG. 16, which illustrates a cross-sectional view of the needle 500 through the line 16-16 shown in FIG. 15, the needle tip 505 is shaped and sized to be received inside the sheath tip 325. In particular, the needle tip 505 is shaped and sized to be snugly received inside the distal portion 410 of the sheath tip 325. In the pictured embodiment, the inner diameter D7 of the distal portion 410 of the sheath tip 325 is sized to be only slightly larger than the outer diameter D8 of the needle tip 505, thereby allowing the needle tip 505 to be securely supported within the sheath tip 325. The needle tip 505 includes an inner diameter D9. The inner diameter D9 of the needle tip 505 may range from 0.20 inches to 0.055 inches. For example, in one embodiment, the inner diameter D9 of the needle tip 505 is 0.035 inches (0.098 cm). The above dimensions are provided for exemplary purposes only, and are not intended to be limiting. Other dimensions are contemplated.

In FIG. 15, the length L8 represents the length of the rigid section 507 of the distal portion 305 of the needle system 300 when the needle 500 is in an extended position. In particular, the rigid section 507 includes the rigid tube portion 390 of the elongate tube 320, the sheath tip 325, and an unsheathed distal part 530 of the needle tip 505. When the needle tip 505 is in an extended condition outside of the outer sheath 310, the length L8 of the rigid section 507 comprises the length LS of the rigid tube portion 390 of the elongate tube 320 in addition to the length L3 of the sheath tip 325 as well as a length L10 of the unsheathed part 530 of the needle 500. Thus, when the needle tip 505 is unsheathed from the outer sheath 310, the length LS of the rigid section 507 may range from 0.20 inches to 0.70 inches. For example, in one embodiment, the length LS measures 15 mm when the needle tip 505 is extended distally from the outer sheath 310. The above dimensions are provided for exemplary purposes only, and are not intended to be limiting. Other dimensions are contemplated. In the pictured embodiment, when the needle 500 is in an extended configuration, a proximal part 531 of the needle tip 505 remains within the outer sheath 310. In particular, the proximal part 531 remains within the rigid tube portion 390.

A length L9 represents the total length of the elongate tube 320, the sheath tip 325, and the unsheathed portion 530 of the needle 500. The length L9 may range from 0.3 inches to 1.5 inches. For example, in one embodiment, the length L9 measures 30 mm. The above dimensions are provided for exemplary purposes only, and are not intended to be limiting. Other dimensions are contemplated.

As shown in FIGS. 14, 17, and 18, the needle jacket 510 comprises a dual lumen, flexible tube. In the pictured embodiment, the needle jacket includes a sensor lumen 550 and a needle lumen 555. The sensor lumen 550 is configured to carry the sensor system 235 shown in FIG. 2. The sensor lumen 550 is blocked (e.g., plugged) at its distal end by a plug element 560. Thus, the sensor lumen 550 is not in fluid communication with the needle tip lumen 512 (shown in FIG. 16), and the sensor system 235 is protected from the contents of the needle lumen 555. The plug element 560 may be positioned as close to the needle tip 505 as possible, thereby maximizing the sensing range of the sensor system 235 relative to the needle 500. In some embodiments, the needle jacket 510, the plug element 560, and the sensor system 235 are configured such that the sensor system 235 includes a positional/orientation sensor (e.g., a 5-DOF sensor) positioned as close to the needle tip 505 as possible to accurately indicate the position of the needle tip 505. In one aspect, the sensor lumen 550 is shaped and configured to minimize bending strain on the sensor system 235 (e.g., to minimize bending strain on a 5-DOF sensor). In one aspect, the needle jacket 510 is shaped and configured to maintain the axial position of the sensor system 235 within 1 mm (relative to the needle lumen).

The needle lumen 555 is configured to be in fluid communication with the needle tip lumen 512. In various instances, the needle lumen 555 may operate as an aspiration lumen, a flow lumen (e.g., an irrigation lumen or a drug delivery lumen), and/or a tool delivery lumen. The needle lumen 555 has a cross-sectional sample area A1. The cross-sectional sample area A1 of the needle lumen 555 may range from 0.1 mm² to 0. mm². For example, in one embodiment, the cross-sectional sample area A1 of the needle lumen 555 is 0.25 mm². The needle jacket 510 may be formed of any of a variety of flexible materials having the requisite flexibility and durability, such as, by way of non-limiting example, polyimide, polyethylene, polyurethane, and fluorinated ethylene propylene.

The needle jacket 510 includes an outer diameter D10. The outer diameter D10 of the 15 needle jacket 510 may range from 0.031 inches to 0.07 inches. For example, in one embodiment, the outer diameter D10 of the needle jacket 510 is 0.050 inches (0.127 cm). The needle jacket 510 includes a thickness T2. The thickness T2 of the needle jacket 510 may range from 0.02 inches to 0.010 inches. For example, in one embodiment, the thickness T2 of the needle jacket 510 is 0.0030 inches (0.0076 cm). The above dimensions are 20 provided for exemplary purposes only, and are not intended to be limiting. Other dimensions are contemplated.

As shown in FIGS. 19A and 19B, the ability to decrease the length L8 of the rigid section 507 of the needle system 300 by telescoping the needle tip 505 into the rigid section 507 allows the needle system 300 to navigate a tortuous pathway 560 (e.g., having a narrow turn radius) with the needle 500 in a sheathed condition while still allowing for the structural characteristics (e.g., length and diameter) of the needle tip 505 necessary to penetrate a target area or lesion 565 inside the patient.

FIG. 19A illustrates the needle system 300 navigating a sharp, narrow bend in the tortuous passageway 560. Because the needle tip 505 is in a telescoped or retracted 3 0 configuration in which the needle tip 505 is retracted within the rigid section 507 of the outer sheath 310, the length L8 of the rigid section 507 is minimized (i.e., as shown in FIG. 14, and as compared to the length L8 shown in FIGS. 15 and 19A when the needle tip 505 is in an extended configuration). The shortened length L8 of the rigid section 507 allows the needle system 300 to navigate narrow or tight bends in the tortuous pathway 560 without inadvertently injuring neighboring tissue.

FIG. 19B illustrates the needle tip 505 extending out of the outer sheath 310 and penetrating the target area 565 (e.g., to obtain or aspirate a biopsy sample from the target area 565). In some embodiments, the needle system 300 aspirates a biopsy sample of the target 5 area 565 into the needle lumen 555 shown in FIGS. 14 and 15. In other embodiments, the needle system 300 takes a biopsy sample of the target area 565 into the needle tip 505. As the needle system obtains the biopsy sample, the plug element 502 prevents environmental fluid (e.g., tissue and/or blood) from contacting the sensor system 235 contained within the sensor lumen 550 as shown in FIGS. 14 and 15.

When the needle tip 505 is extended past the distal end 355 of the sheath tip 325, the rigid tube portion 390 and the sheath tip 325 cooperate to surround, support, and effectively rigidize the needle tip 505 to enable the needle 500 to penetrate the target area 565. In the pictured embodiment, the combined lengths L5 and L3 of the rigid tube portion 390 and the sheath tip 325, respectively, are long enough to sheath the needle tip 505 when the needle tip 505 is retracted, but short enough to navigate a tight bend in the tortuous pathway 560 (as shown in FIG. 19A). Accordingly, the length LS of the rigid section 507 of the outer sheath 310 is at least as long as the length LN of the needle tip 505 (shown in FIG. 14). In other words, the length LN of the needle tip 505 is equal to or less than the combined lengths L5 and L3 of the rigid tube portion 390 and the sheath tip 325, respectively. Thus, the needle system 300 can telescope inward upon itself enough to sufficiently reduce the length L8 of the rigid portion 507 (as shown in FIG. 14) to navigate a tight bend radius while maintaining the ability to provide enough distal rigidity to provide stability, distance control, target accuracy, and a predictable needle path as the needle tip 505 emerges from the outer sheath 310.

Similarly, as shown in FIGS. 20A and 20B, the ability to decrease the length Lr of the rigid section 284 of the needle system 250 by telescoping the rigid distal section 270 of the needle 265 into the rigid distal portion 280 of the outer sheath 260 allows the needle system 250 to navigate the tortuous pathway 560 with the needle 265 in a sheathed condition while still allowing for the structural characteristics (e.g., length and diameter) of the rigid distal section 270 necessary to penetrate the lesion 565 inside the patient.

FIG. 20A illustrates the needle system 250 navigating a sharp, narrow bend in the tortuous passageway 560. Because the rigid distal section 270 is in a telescoped or retracted configuration in which the rigid distal section 270 is retracted within the rigid distal portion 280 of the outer sheath 260, the length Lr of the rigid section 284 is minimized (i.e., as shown in FIG. 3B, and as compared to the length Lr shown in FIG. 3A when the needle tip 505 is in an extended configuration). The shortened length Lr of the rigid section 284 allows the needle system 250 to navigate narrow or tight bends in the tortuous pathway 560 without inadvertently injuring neighboring tissue.

FIG. 20B illustrates the rigid distal section 270 extending out of the outer sheath 260 and penetrating the target area 565 (e.g., to obtain or aspirate a biopsy sample from the target area 565). In the pictured embodiment, both the rigid distal section 270 and the flexible proximal section 273 of the needle 265 extend outside of the outer sheath 260. In this manner, the needle system 250 allows for both the rigid and flexible sections of the needle 265 to penetrate the lesion 565. In some embodiments, the needle system 250 aspirates a biopsy sample of the target area 565 into the needle lumen 274. In other embodiments, the needle system 250 takes a biopsy sample of the target area 565 into the distal rigid section 270.

When only the distal rigid section 270 is extended past the distal end 276 of the sheath 260, the rigid distal portion 280 surrounds, supports, and effectively rigidize the distal rigid section 270 to enable the needle 265 to penetrate the target area 565. In the pictured embodiment, the length Ld of the rigid distal portion 280 is long enough to sheath the rigid distal section 270 when the needle 265 is retracted, but short enough to navigate a tight bend in the tortuous pathway 560 (as shown in FIG. 20A). Accordingly, the length Ld of the rigid distal portion 280 of the outer sheath 260 is at least as long as the length Ln of the rigid distal section 270 of the needle 265 (as shown in FIG. 3C). Thus, the needle system 250 can telescope inward upon itself enough to sufficiently reduce the length Lr of the rigid section 284 (as shown in FIG. 3B) to navigate a tight bend radius while maintaining the ability to provide enough distal rigidity to provide stability, distance control, target accuracy, and a predictable needle path as the needle 265 emerges from the outer sheath 310.

FIGS. 21-23 illustrate partially cross-sectional side views of a proximal portion 600 of the needle system 300 according to one embodiment of the present disclosure. In some embodiments, the proximal portion 600 may be the same as the proximal portion 233 depicted in FIG. 2. FIG. 21 illustrates the proximal portion 600 of the needle system 300 when both the needle 500 and the outer sheath 310 are in a non-extended or non-advanced condition. The proximal portion 600 includes a needle handle 605, a sheath handle 610, and a stabilizer tube handle 615. The stabilizer tube 620 may comprises a short, thin-walled hypotube that is coupled to another medical instrument (e.g., a catheter or bronchoscope). The needle handle 605, the sheath handle 610, and the stabilizer tube handle 615 are coupled to the proximal ends of the needle 500, the outer sheath 310, and the stabilizer tube 620, respectively. The needle 500, the outer sheath 310, and the stabilizer tube 620 are arranged in a telescopic fashion relative to one another. In particular, the needle 500 is configured to be slidably received within the sheath handle 610 and the outer sheath 310, and the outer sheath 310 is configured to be received within the stabilizer tube handle 615 and the stabilizer tube 620. Thus, in the pictured embodiment, the needle 500 is slidably received within the outer sheath 310, and the outer sheath 310 (i.e., carrying the needle 500) is slidably received within the stabilizer tube 620.

In the pictured embodiment, the needle handle 605 includes a primary port 625 and a secondary port 630. In alternative embodiments, the needle handle 605 may have a different configuration and/or number of ports. The primary port 625 may be used as an aspiration lumen (e.g., for biopsy retrieval) and/or as a delivery lumen (e.g., for delivery of drugs or irrigation fluid). The secondary port 630 may carry wires or other connective elements from the sensor system 108, the actuator 210, and/or the teleoperational platform 215 shown in FIG. 2. In one embodiment, the secondary port 630 carries connective elements from the sensor system 235 shown in FIG. 2.

The needle handle 605 and/or the sheath handle 610 may be inked or otherwise marked with incremental measured markings at their proximal portions to indicate its insertion distance or depth of advancement (e.g., relative to the stabilizer tube 620 and/or the distal end 355 of the sheath tip 325 as shown in FIG. 5). In the pictured embodiment, the needle handle 605 and the sheath handle 610 include markers 632. The markers 632 may extend the length of the needle handle 605 and/or the sheath handle 610. The markers 632 may function as visible insertion distance indicators. In some embodiments, the marker 632 may be radiopaque (e.g., fluoroscopic markers).

In the pictured embodiment, the sheath handle 610 and the stabilizer tube handle 615 include locking elements 635a, 635b, respectively. The locking elements 635a, 635b enable a user to selectively stop the advancement or extension of the needle 500, the outer sheath 310, or both. In the pictured embodiment, the locking elements 635a, 635b are in the form of locking screws. For example, upon tightening a locking screw 635a, the user can halt the distal advancement of the needle 500 into the sheath handle 610 and the outer sheath 310. By tightening the locking screws 635a, 635b, the user can temporarily lock the relative positions of the needle 500 and the outer sheath 310 in a desired arrangement (e.g., depending upon the real-time requirements of the medical intervention). Locking elements 635a,635b are just one example of a manual locking mechanism operable to temporarily lock the relative positions of moveable elements in a desired position. In other embodiments, the relative positions of moveable elements can be locked in a different way. Locking element 635a is one example of a holding mechanism that maintains the position of the needle 500 relative to the outer sheath 310. In one aspect, locking element 635a maintains the needle 500 in an extended position relative to the outer sheath 310. In other embodiments, the relative position of the needle 500 and the outer sheath 310 may be maintained in a different way.

FIG. 22 illustrates the proximal portion 600 of the needle system 300 when the needle 500 is in an extended or advanced condition and the outer sheath 310 is in a non-extended or non-advanced condition. The needle handle 605 is shown pushed or advanced distally such 10 that the needle handle 605 partially telescopes into the sheath handle 610. As the needle handle 605 is advanced distally, the needle 500 simultaneously advances distally into the outer sheath 310. As the needle 500 advances distally through the outer sheath 310, the needle tip 505 of the needle 500 can emerge from the sheath tip 325 (as also shown in FIG. 15). In one example, the needle 500 is inserted a minimum of 30 mm.

FIG. 23 illustrates the proximal portion 600 of the needle system 300 when both the needle 500 and the outer sheath 310 are in an extended or advanced condition. As shown in FIG. 23, the needle handle 605 is shown pushed or advanced distally such that the needle handle 605 partially telescopes into the sheath handle 610. In addition, the sheath handle 610 is shown pushed or advanced distally such that the sheath handle 610 partially telescopes into the stabilizer tube handle 615. As the sheath handle 605 is advanced distally, the outer sheath 310 simultaneously advances distally (e.g., through the stabilizer tube 620). As the outer sheath 310 advances distally over the needle 500, the sheath tip 325 and the elongate tube 320 of the outer sheath 310 surround and sheath the needle tip 505 of the needle 500 (as also shown in FIG. 14).

In one instance, the user may advance the needle system 300 (as shown in FIG. 14) through the stabilizer tube 620 and any intervening medical instrument toward an anatomical area of interest within a patient while the needle 500 is sheathed within the outer sheath 310. During this initial advancement, the proximal portion 600 of the needle system 300 may appear as shown in FIG. 22. In one aspect, the user can utilize the sensor system 235 (shown 3 0 in FIG. 2) to accurately position the distal end 355 of the sheath tip 325 adjacent an anatomical area of interest (e.g., within a patient). After positioning the distal end 355 of the sheath tip 325 adjacent an anatomical area of interest, the user may distally advance the needle handle 605 into the sheath handle 610, thereby causing the needle tip 505 of the needle 500 to emerge from the outer sheath 310 as shown in FIG. 14 (e.g., and penetrate tissue distal of the outer sheath 310). As or after the user advances the needle 500 into the tissue, the user may distally advance the sheath handle 610 to slide the outer sheath 310 over the needle tip 505. The outer sheath 310 can protect the needle tip 505 and further guide the trajectory of the needle 500 as the needle tip 505 progresses through the tissue (as shown in FIG. 20).

In another instance, for example during a biopsy procedure, the user may withdraw the needle 500 from the outer sheath 310 after obtaining a biopsy (e.g., within the needle tip 505 and/or the needle lumen 555) while leaving the outer sheath 310 (e.g., the sheath tip 325) in position adjacent the anatomical area of interest (e.g., the lesion 565 shown in FIGS. 18 and 10 19). Thus, the user can examine whether a desirable biopsy sample has been obtained without removing the outer sheath 310 and losing the location of the first biopsy. If the user desires another biopsy sample from the same biopsy location or adjacent that biopsy location, the user can simply reinsert the needle 500 into the outer sheath 310 and advance the needle handle 605 distally as shown in FIG. 22 to obtain another biopsy sample.

In other embodiments, the needle system may include multiple sheaths or rigid sections arranged in a telescoping fashion about the needle 500. Such sheaths may be substantially similar in design to the outer sheath 310, and such rigid sections may be substantially similar in design to the rigid section 507 described above. FIGS. 24 and 25 illustrate a needle system 700 that includes a rigid section 705, and a rigid section 710, a rigid section 715, and the needle 500 arranged in a telescoping fashion relative to one another. In particular, the needle 500 is configured to be slidably retracted and received within the rigid section 715, the rigid section 715 is configured to be slidably retracted and received within the rigid section 710, and rigid section 710 is configured to be slidably retracted and received within the rigid section 705. In FIG. 24, the needle 500 and the rigid sections 715 and 710 are shown in an extended or partially extended condition with an overall rigid length L11 of the needle system 700. However, as shown in FIG. 25, the needle 500, the rigid section 715, and/or the rigid section 710 can telescope inwardly (either together or independently) in the direction of arrows 725 to shorten the rigid length L11 of the needle system to a length L12 of the rigid section 705. In some embodiments, the needle system includes multiple telescoping portions having both flexible and rigid portions.

FIG. 26 illustrates an exemplary needle system 790 according to one embodiment of the present disclosure. In particular, the exemplary needle system 790 includes an exemplary sensor stylet 800 positioned within an exemplary medical instrument 805 according to one embodiment of the present disclosure. In the pictured embodiment, the medical instrument 805 comprises a needle with a bevel tip 810. However, in other embodiments, the medical instrument 805 may comprise any of a variety of hollow medical instruments including a lumen 815, including, by way of non-limiting example, an endoscope, a catheter, a biopsy tool, and a delivery instrument. In some embodiments, the medical instrument 805 may be the same as the needle 265 shown in FIGS. 3A-3C, as described below with reference to FIG. 27.

The sensor stylet 800 is a removable stylet that is shaped and sized to be slidably received within the lumen 815 of the medical instrument 805. The sensor stylet 800 comprises an elongate member that includes an outer diameter Ds that is less than an inner luminal diameter Di of the lumen 815 of the medical instrument 805. In some embodiments, the outer diameter Ds measures only slightly less than the luminal diameter Di such that the sensor stylet 800 fits flushly within the medical instrument 805.

The sensor stylet 800 includes a sensor system 820 configured to provide shape and/or positional data regarding the medical instrument 805. In some embodiments, the sensor system 820 may be the same as the sensor system 235 described above. The sensor system 235 is substantially aligned with at least a portion of the sensor stylet 800. If the needle system 790 is the medical instrument system 104 of the teleoperational medical system 100 shown in FIG. 1, the sensor system 235 may be a component of the sensor system 108. If the needle system 790 is manually operated or otherwise used for non-robotic procedures, the sensor system 235 may be coupled to a tracking system that interrogates a shape sensor and processes the received shape data. Regardless of the specific steering mechanism of the medical instrument 805, the usability of the needle system 790 is enhanced by the inclusion of the sensor system 235.

The sensor system 235 can measure or detect characteristics of the medical instrument 805. For example, the sensor system 235 can determine the position, orientation, speed, pose, and/or shape of the medical instrument 805 and/or of one or more discrete segments along the medical instrument 805. The data read by the sensor system 235 can be converted into useable shape and/or positional information by the sensor system 108 and/or the control system 112 shown in FIG. 1. The shape and/or positional information can then be used to guide further manipulation of the medical instrument 805. In the pictured embodiment, the sensor system 235 terminates proximal to a distal end 822 of the sensor stylet 800. In other embodiments, the sensor system 235 may extend to the distal end 822 of the sensor stylet 800.

In certain embodiments, the sensor stylet 800 may include radiopaque markers. For example, in the embodiment shown in FIG. 26, the sensor stylet 800 includes a radiopaque marker 825 coupled a distal portion 830 of the sensor stylet 800. The radiopaque marker 825 comprises a tubular marker that circumferentially surrounds the sensor stylet 800. In other embodiments, the radiopaque markers may be shaped and configured in any of a variety of suitable shapes, including, by way of non-limiting example, rectangular, triangular, ovoid, linear, and non-circumferential shapes.

The radiopaque marker 825 permits the user to fluoroscopically visualize the location and orientation of the sensor stylet 800 (and of the medical instrument 805 if the sensor stylet 800 is positioned within the lumen 815) within the patient. The radiopaque marker 825 may be formed of any of a variety of biocompatible radiopaque materials that are sufficiently visible under fluoroscopy to assist in the medical procedure involving the medical instrument 805. Such radiopaque materials may be fabricated from, by way of non-limiting example, platinum, gold, silver, platinum/iridium alloy, and tungsten. For example, in the pictured embodiment, the radiopaque marker 825 may be formed of tungsten.

The marker 825 may be attached to the sensor stylet 800 using a variety of known methods such as adhesive bonding, lamination between two layers of polymers, or vapor deposition, for example. In some embodiments, the radiopaque marker 825 is formed by a platinum coating or cladding. Though the pictured embodiment includes a single radiopaque marker 825 arranged adjacent the distal end 822 of the sensor stylet 800, other embodiments may include any number and arrangement of radiopaque markers. In some embodiments, the sensor stylet 800 lacks radiopaque markers.

The medical instrument 805 may be formed of various metals, alloys, composites, or plastics, among others. For example, the medical instrument 805 may be formed of surgical steel, biocompatible plastic, or combinations, among others. The sensor stylet 800 may also be formed of various metals, alloys, composites, plastics, or combinations, among others. For example, the sensor stylet 800 may be formed of surgical steel or biocompatible plastic among others. In addition, the medical instrument 805 and sensor stylet 800 may have cross-sections with various shapes, in one exemplary embodiment, the medical instrument 805 may be formed of surgical steel and the sensor stylet 800 may include a surgical steel tip and coil. In this exemplary embodiment, the medical instrument 805 and sensor stylet 800 have a cylindrical shape and circular cross section.

The sensor stylet 800 may be selectively inserted into the lumen 815 of the medical instrument 805 (e.g., through a proximal end (not shown) of the medical instrument 805) when the user desires to employ the stylet, may be removed when the sensor stylet 800 is no longer needed to allow for the use of the lumen 815 (e.g., for aspiration or delivery), and may be reinserted into the lumen 815 if the sensor stylet 800 is needed again. In the pictured embodiment, at least a portion of the sensor stylet 800 is aligned with a longitudinal axis LA of the medical instrument 805 when the sensor stylet 800 is positioned within the lumen 815. The sensor stylet 800 may have varying degrees of flexibility along its length. In one embodiment, for example, the sensor stylet 800 may be more rigid at its distal end than at its proximal end. In other embodiments, the sensor stylet 800 may be of uniform flexibility along its length.

FIG. 27 illustrates the sensor stylet 800 shown in FIG. 26 positioned within the exemplary needle system 250 shown in FIGS. 3A-3C. In particular, the sensor stylet 800 is shown positioned within the lumen 274 of the needle 265. Thus, the sensor stylet 800 may assist in guiding the needle system 250 through patient anatomy as shown in FIGS. 20A and 20B by providing shape and/or position data about the needle 265 as the needle 265 traverses the patient anatomy.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical device comprising:
   an elongate sheath comprising a distal portion and a proximal portion, the elongate sheath defining a first lumen;
   an elongate instrument slidably disposed at least partially within the first lumen, the elongate instrument comprising a rigid distal section, the rigid distal section defining a second lumen;
   a first extension member coupled to a proximal end of the elongate instrument;
   a second extension member coupled to a proximal end of the elongate sheath, the second extension member configured to at least partially receive the elongate instrument; and
   a protrusion coupled to the second extension member, the protrusion movable in a direction transverse to a longitudinal axis of the second extension member, movable within an opening defined by the second extension member, and configured to maintain the first extension member in a rotationally fixed position relative to the second extension member during axial movement of at least the first extension member.

2. The medical device of claim 1, wherein the rigid distal section is retractable into the elongate sheath.

3. The medical device of claim 1, wherein a length of the rigid distal section is less than a length of the distal portion.

4. The medical device of claim 1, wherein the elongate instrument is configured to receive a biopsy sample of an anatomical target via the second lumen.

5. The medical device of claim 1, wherein a longitudinal axis of the first extension member is parallel with the longitudinal axis of the second extension member.

6. The medical device of claim 1, wherein the second extension member includes at least one insertion distance indicator configured to indicate an insertion distance of the elongate instrument relative to the elongate sheath.

7. The medical device of claim 6, wherein the at least one insertion distance indicator is positioned on an outside surface of the second extension member.

8. The medical device of claim 6, wherein the at least one insertion distance indicator is configured to provide a visual indication of the insertion distance of the elongate instrument relative to the elongate sheath.

9. The medical device of claim 1, wherein the second extension member includes a plurality of insertion distance indicators configured to indicate an insertion distance of the elongate instrument relative to the elongate sheath, wherein each insertion distance indicator of the plurality of insertion distance indicators is spaced from an adjacent insertion distance indicator of the plurality of insertion distance indicators by an equal incremental distance.

10. The medical device of claim 9, wherein each insertion distance indicator is spaced along the longitudinal axis of the second extension member.

11. The medical device of claim 1, wherein at least a proximal section of the elongate instrument is configured to be positioned within the elongate sheath.

12. The medical device of claim 11, wherein at least the proximal section of the elongate instrument is slidable within the elongate sheath.

13. The medical device of claim 1, wherein the elongate instrument is configured to be extended from the elongate sheath via an actuator of a manipulator.

14. The medical device of claim 1, further comprising a sensor system configured to measure a shape of the elongate instrument or a position of the elongate instrument.

15. The medical device of claim 1, wherein the protrusion is further configured to maintain the rigid distal section of the elongate instrument in an extended position from the distal portion of the elongate sheath.

16. The medical device of claim 1, wherein a longitudinal axis of the protrusion is transverse to the longitudinal axis of the second extension member.

* * * * *